United States Patent
Kawada et al.

(10) Patent No.: US 9,927,298 B2
(45) Date of Patent: Mar. 27, 2018

(54) SPECTROSCOPIC MEASUREMENT APPARATUS

(71) Applicant: HAMAMATSU PHOTONICS K.K., Hamamatsu-shi, Shizuoka (JP)

(72) Inventors: Yoichi Kawada, Hamamatsu (JP); Yoshiyuki Shimizu, Hamamatsu (JP); Toyohiko Yamauchi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 37 days.

(21) Appl. No.: 15/131,390

(22) Filed: Apr. 18, 2016

(65) Prior Publication Data

US 2016/0313182 A1 Oct. 27, 2016

(30) Foreign Application Priority Data

Apr. 22, 2015 (JP) .................. 2015-087407

(51) Int. Cl.
| | |
|---|---|
| *G01J 3/02* | (2006.01) |
| *G01J 3/42* | (2006.01) |
| *G01N 21/35* | (2014.01) |
| *G01J 3/12* | (2006.01) |

(52) U.S. Cl.
CPC .............. *G01J 3/0229* (2013.01); *G01J 3/42* (2013.01); *G01J 2003/1213* (2013.01); *G01N 2021/3595* (2013.01)

(58) Field of Classification Search
CPC ............................................ G01N 2021/3595
See application file for complete search history.

(56) References Cited

U.S. PATENT DOCUMENTS

| | | | |
|---|---|---|---|
| 7,342,658 B2 * | 3/2008 | Kowarz .................... | G01J 3/02 356/300 |
| 2014/0022542 A1 * | 1/2014 | Otera ........................ | G01J 3/42 356/300 |
| 2015/0355081 A1 * | 12/2015 | Phillips .............. | G01N 21/3504 356/451 |

FOREIGN PATENT DOCUMENTS

| | | |
|---|---|---|
| JP | 2001-108613 A | 4/2001 |
| JP | 4508476 B2 | 7/2010 |
| JP | 5591680 B2 | 9/2014 |

* cited by examiner

*Primary Examiner* — Shawn Decenzo
(74) *Attorney, Agent, or Firm* — Drinker Biddle & Reath LLP

(57) ABSTRACT

A spectroscopic measurement apparatus includes a light source, a diffraction grating being a spectroscopic unit, a spatial filter unit, a detection unit, and an analysis unit. The diffraction grating spatially disperses light from the light source, and outputs the light to different optical paths according to a wavelength. The spatial filter unit inputs the light from the diffraction grating to different positions according to the wavelength, applies loss depending on the wavelength to the light, and outputs the light. The detection unit detects the intensity of the light from the spatial filter unit. The analysis unit obtains the intensities of light in an absorption band and light in a non-absorption band of a component in a measurement sample on an optical path between the light source and the detection unit based on the detection result, and evaluates the component in the measurement sample.

9 Claims, 29 Drawing Sheets

SPECTROSCOPIC MEASUREMENT APPARATUS

BACKGROUND OF THE INVENTION

Field of the Invention

The present invention relates to a spectroscopic measurement apparatus.

Related Background Art

In an infrared range, in particular, a region having a wavelength of 2.5 to 25 μm is referred to as a fingerprint region, and an absorption peak specific to a substance appears in the region, therefore, the region is used to identify the substance. When absorption characteristics of the substance in the infrared range are measured, Fourier transform infrared spectroscopy (FTIR) technique is mainly used.

In the FTIR, a measurement sample is arranged on one optical path of two optical paths in an interference optical system, and an optical path length difference between the two optical paths is scanned so that interference intensity data is obtained in time series, and by performing Fourier transform to the time series data, absorption information on the measurement sample in each wavelength is obtained. For this reason, the FTIR needs a huge amount of time series data to obtain detailed information on the measurement sample. However, due to the property of a laser light source used as a light source, the number of data obtained per unit time is limited. Since it is necessary to perform measurement for a long time in order to increase the number of data, it is difficult to perform high-speed measurement.

On the other hand, a dispersion type spectroscopic measurement apparatus has been known other than the FTIR. The dispersion spectroscopic measurement apparatus detects the intensity of the light in each wavelength by a detector by spatially dispersing the light which has passed through the measurement sample by a spectroscopic unit and propagating the light to different optical paths according to the wavelength, and then, the apparatus obtains the absorption information on the measurement sample in each wavelength. The intensities of the light components in a plurality of wavelengths can be simultaneously detected by using a plurality of detectors, and therefore, high-speed measurement can be performed. However, it is necessary to use the detector corresponding to each wavelength. Since it is necessary to use many detectors to obtain the detailed absorption information on the measurement sample, the apparatus gets to be expensive.

An apparatus disclosed in Patent Document 1 is for measuring a cholesterol concentration, and by using a plurality of bandpass filters having different transmission wavelength bands from each other as sequentially switching them, absorption information on the measurement sample (cholesterol) in each wavelength is obtained, and the cholesterol concentration is measured. However, since it is necessary to sequentially switch many bandpass filters, it is difficult to perform high-speed measurement.

An apparatus disclosed in Patent Document 2 is for identifying a tooth color based on spectroscopic characteristics of teeth, and by using a filter having loss characteristics according to the spectroscopic characteristics in the measurement sample (teeth), the color of the measurement sample (tooth) is classified from light intensity measurement data measured a few times. However, it is difficult to product the filter according to the measurement sample, and also, there is a possibility that the apparatus becomes expensive.

An apparatus disclosed in Patent Document 3 is for measuring an amount of atmospheric gas, and by combining an etalon, a bandpass filter, and a spatial dispersion by a diffraction grating, a change in an absorbance in an absorption wavelength of the measurement sample (atmospheric gas) is compared with the intensity of the wavelength (window band) which is not absorbed by the measurement sample, and then, the apparatus constantly monitors the atmospheric gas amount.

The apparatus disclosed in Patent Document 3 measures the absorbance in a specific single absorption wavelength of the measurement sample. In the evaluation of the kind of a part of the atmospheric gas, only when it is not necessary to consider another substance having absorption in the same band, the amount can be evaluated by measuring the absorbance in a single wavelength. However, when the absorption wavelength of the measurement sample is similar to or same as the absorption wavelength of another sample, the samples cannot be distinguished (identified).

Patent Document 1: Japanese Patent Publication No. 5591680

Patent Document 2: Japanese Patent Publication No. 4508476

Patent Document 3: Japanese Patent Application Laid-Open Publication No. 2001-108613

SUMMARY OF THE INVENTION

The present invention has been made in order to solve the above problem, and an object thereof is to provide a spectroscopic measurement apparatus which can perform high-speed measurement with an inexpensive configuration.

A spectroscopic measurement apparatus according to the present invention includes (1) a light source outputting light, (2) a spectroscopic unit spatially dispersing the light output from the light source, and outputting the light to different optical paths according to a wavelength, (3) a spatial filter unit inputting the light output from the spectroscopic unit to different positions according to the wavelength, applying loss depending on the wavelength to the light, and outputting the light, (4) a detection unit detecting the intensity of the light output from the spatial filter unit, and (5) an analysis unit obtaining the respective intensities of light in an absorption band and light in a non-absorption band of a component in a measurement sample in the light which has passed through or has been reflected by the measurement sample arranged on an optical path between the light source and the detection unit based on the detection result by the detection unit, and evaluating the component in the measurement sample.

According to the present invention, high-speed measurement can be performed with an inexpensive configuration.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE EMBODIMENTS

Embodiments of the present invention will be described in detail below with reference to the attached drawings. In the description on the drawings, the same elements will be denoted with the same reference symbols, and overlapping description will be omitted.

Figure 1:
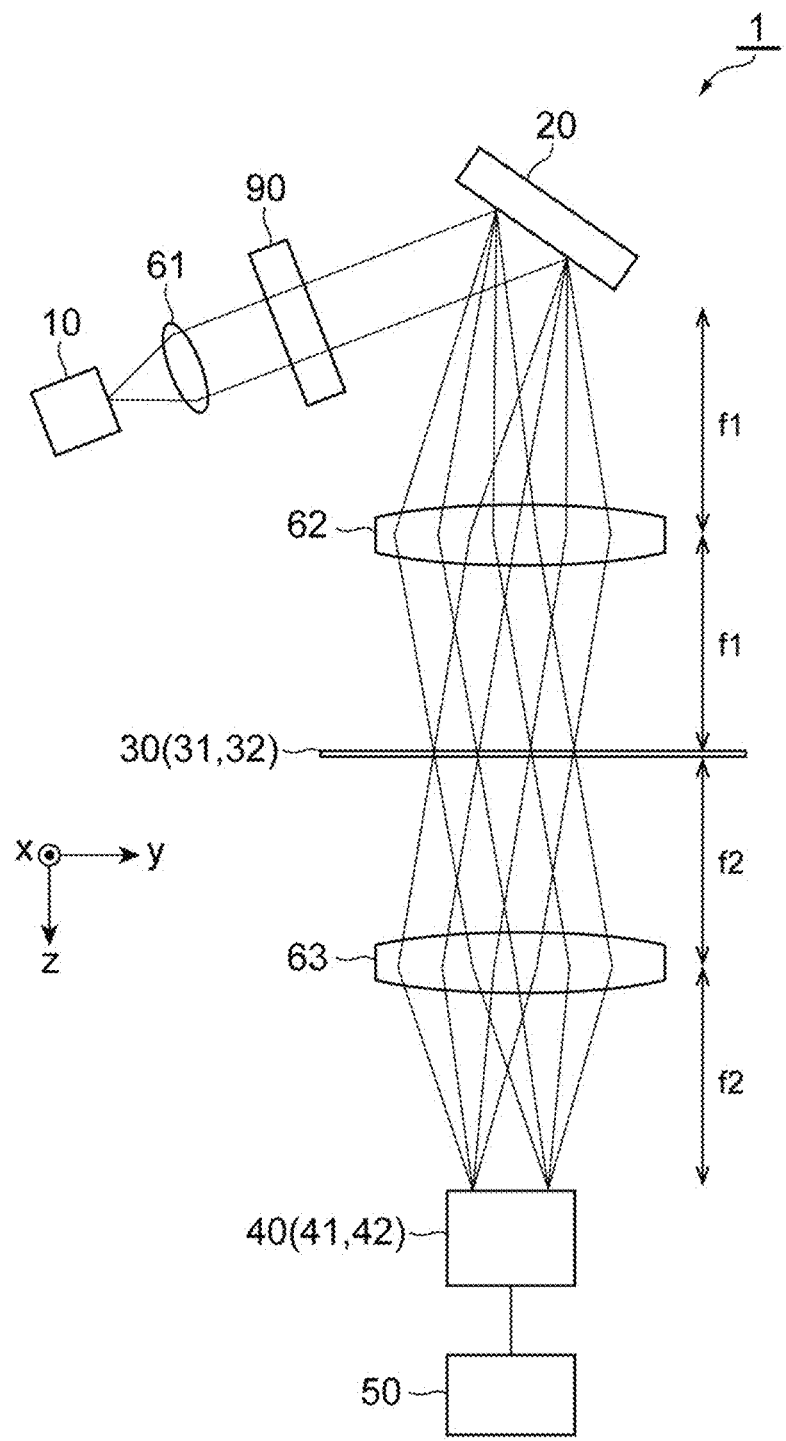
FIG. 1 is a diagram of a configuration of a spectroscopic measurement apparatus 1 according to the present embodiment.
Figure 2:
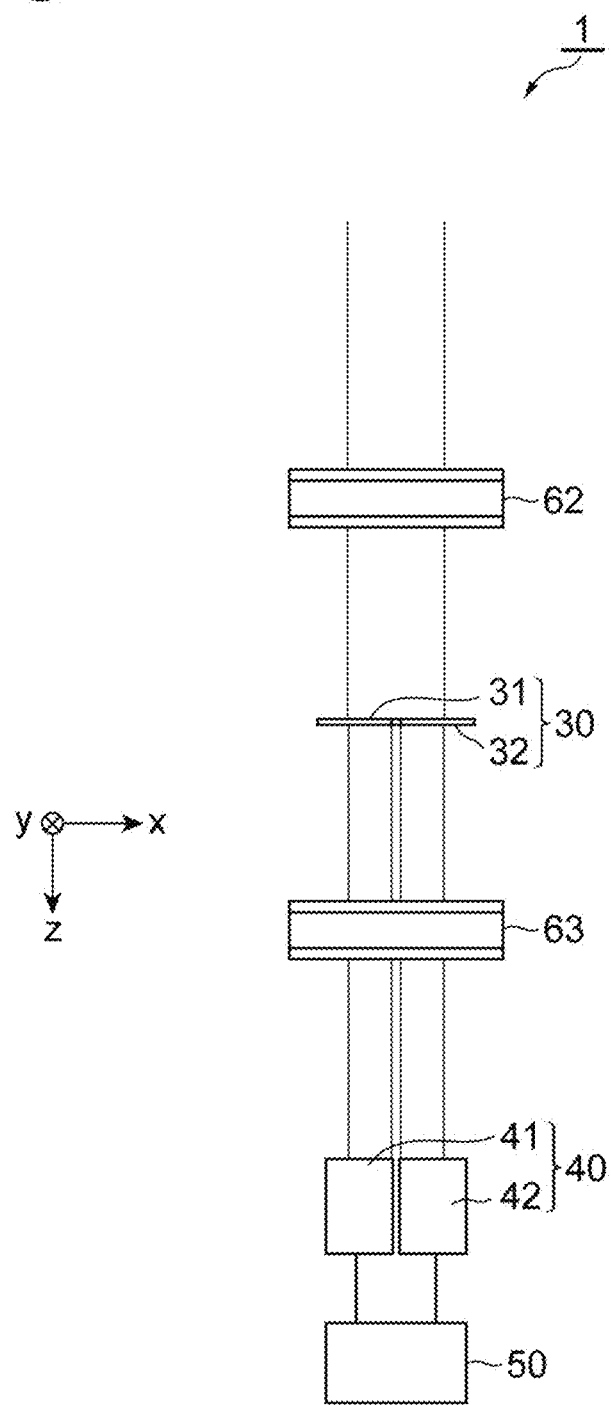
FIG. 2 is a side view of a part of the configuration of the spectroscopic measurement apparatus 1 according to the present embodiment.
Figure 3:
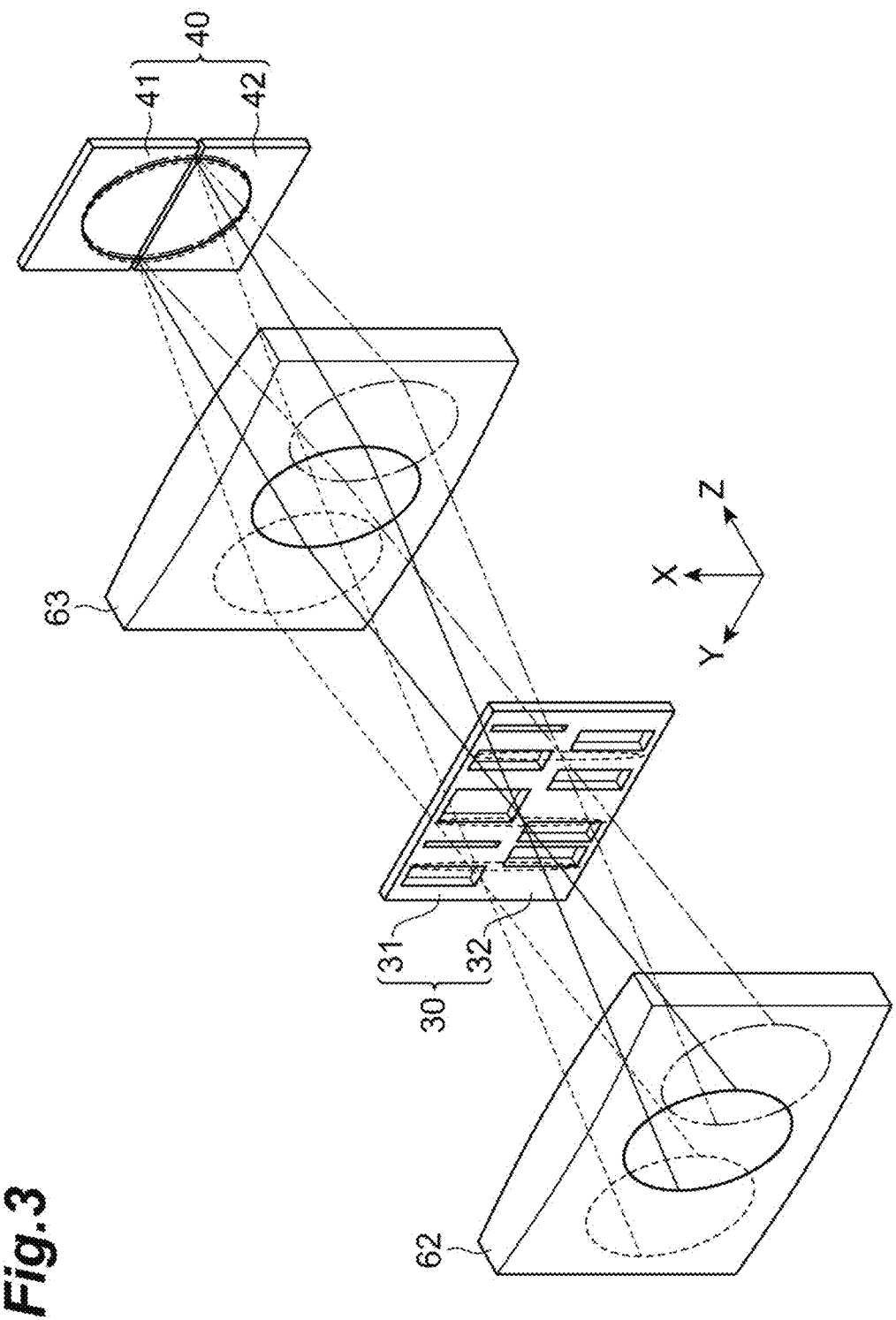
FIG. 3 is a perspective view of a part of the configuration of the spectroscopic measurement apparatus 1 according to the present embodiment.

FIG. 1 to FIG. 3 are diagrams of a configuration of a spectroscopic measurement apparatus 1 according to the present embodiment. For convenience of the description, a xyz orthogonal coordinate system is illustrated in these figures. The spectroscopic measurement apparatus 1 includes a light source 10, a diffraction grating 20, a spatial filter unit 30, a detection unit 40, an analysis unit 50, a lens 61, a cylindrical lens 62, and a cylindrical lens 63, and spectroscopically measures a measurement sample 90 arranged on an optical path between the light source 10 and the detection unit 40.

FIG. 2 is a side view of a part of the configuration of the spectroscopic measurement apparatus 1 according to the present embodiment. FIG. 1 shows the configuration of the spectroscopic measurement apparatus 1 viewed in an x axis direction perpendicular to an optical axis (z axis) of an optical system from the diffraction grating 20 to the detection unit 40. FIG. 2 shows the configuration of the spectroscopic measurement apparatus 1 viewed in a y axis direction perpendicular to both the z axis and the x axis. Further, FIG. 3 is a perspective view of a part of the configuration of the spectroscopic measurement apparatus 1 according to the present embodiment.

The light source 10 outputs light. The light source 10 outputs light in a wavelength band suitable for spectroscopically measuring of the measurement sample 90. It is preferable that the light source 10 output light in an infrared range (in particular, a region of wavelength of 2.5 to 25 μm which is fingerprint region), however, the light source is not limited to this. For example, a lamp light source, a quantum cascade laser, and a thermal light source and the like are used as the light source 10. The lens 61 collimates the light output from the light source 10.

The diffraction grating 20 inputs light which has passed through the measurement sample 90 in the light collimated by the lens 61. The diffraction grating 20 acts as a spectroscopic unit which spatially disperses the input light and outputs light components to the different optical paths according to the wavelength. It is assumed that the light input to the diffraction grating 20 be propagated in parallel to an yz plane, and that the light output from the diffraction grating 20 also be propagated in parallel to the yz plane. The light component output from the diffraction grating 20 is propagated in a direction which is different according to the wavelength.

The cylindrical lenses 62 and 63 have condensing actions in the y axis direction. The diffraction grating 20 is arranged at a front focal point position of the cylindrical lens 62. The spatial filter unit 30 is arranged at a rear focal point position of the cylindrical lens 62 and a front focal point position of the cylindrical lens 63. The detection unit 40 is arranged at a rear focal point position of the cylindrical lens 63.

Therefore, the spatial filter unit 30 inputs the light output from the diffraction grating 20 to different positions according to the wavelength. Then, the spatial filter unit 30 applies loss depending on the wavelength to the light and outputs the light. Further, the detection unit 40 detects the intensity of the light output from the spatial filter unit 30. As the detection unit 40, a unit having a sensitivity in a band of the light output from the light source 10 is used, and for example, an MCT (mercury cadmium telluride) detector and a thermal detector such as a bolometer are used.

The analysis unit 50 obtains the respective intensities of the light in an absorption band and the light in a non-absorption band of the component in the measurement sample 90, based on the detection result by the detection unit 40, and evaluates the component in the measurement sample 90. For example, a computer having a CPU and a memory is used as the analysis unit 50.

Figure 29:
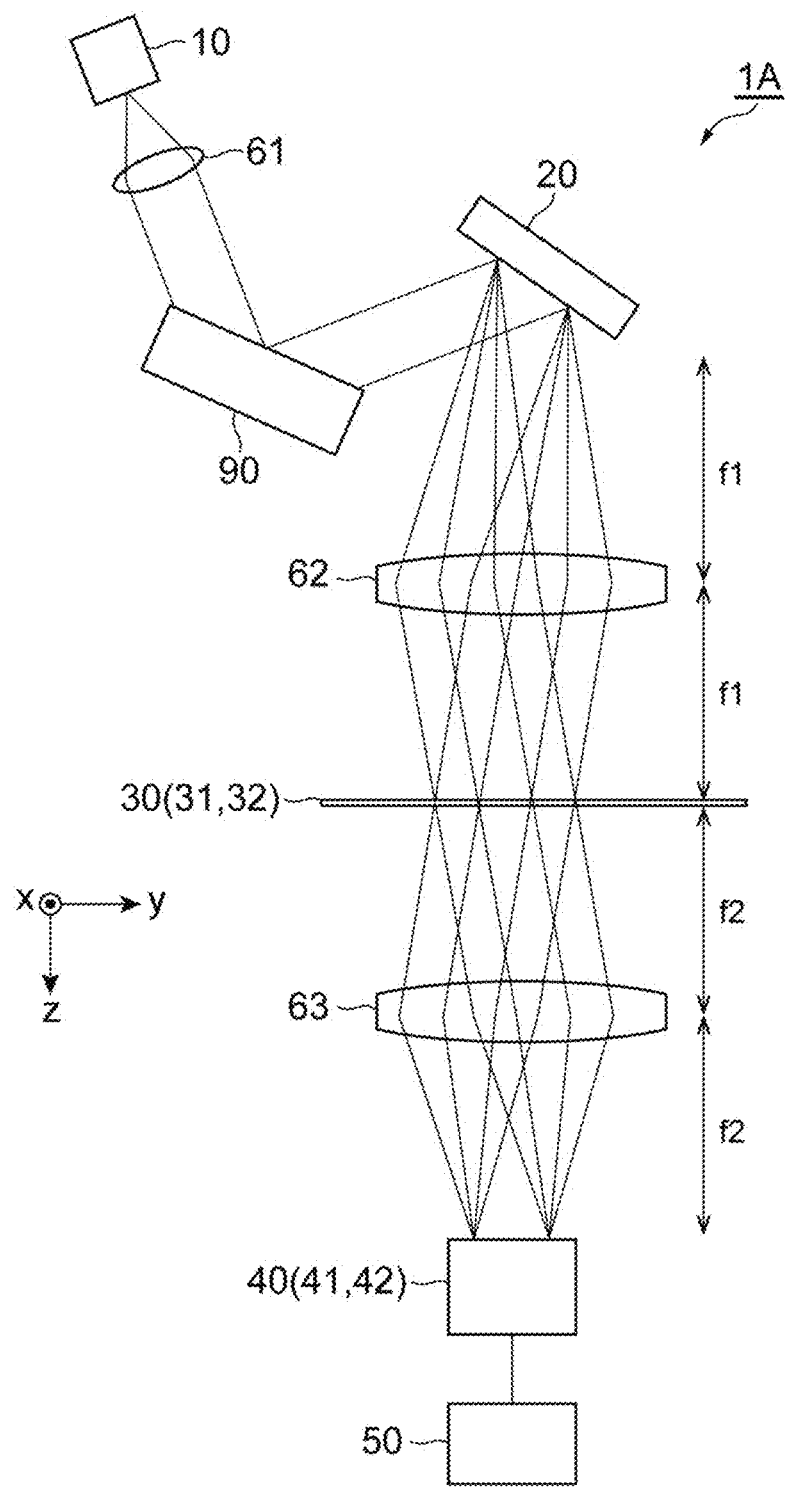
FIG. 29 is a diagram of a configuration of a spectroscopic measurement apparatus 1A according to a modification of the present embodiment.

In FIG. 1, the measurement sample 90 is arranged on the optical path between the lens 61 and the diffraction grating 20, however, the arrangement is not limited to this, and it is sufficient that the measurement sample 90 be arranged on the optical path between the light source 10 and the detection unit 40. In FIG. 1, the light which has passed through the measurement sample 90 is detected, however, as in a configuration of a spectroscopic measurement apparatus 1A illustrated in FIG. 29, light reflected by the measurement sample 90 may be detected.

The reflection type diffraction grating is illustrated as the diffraction grating 20 in FIG. 1, however, a transmission type diffraction grating may be used. The transmission type spatial filter unit 30 is illustrated in FIG. 1, however, a reflection type spatial filter unit may be used. The transmission type lens is used in FIG. 1, however, a reflection type light condensing curved surface mirror may be used.

As illustrated in FIG. 2 and FIG. 3, the spatial filter unit 30 includes a first filter 31 and a second filter 32 arranged at different positions from each other in the x axis direction. The first filter 31 selectively applies loss to the light in the absorption band of the component in the measurement sample 90. The second filter 32 selectively applies loss to the light in the non-absorption band of the component in the measurement sample 90.

Further, the detection unit 40 includes a first detector 41 and a second detector 42 arranged at different positions from each other in the x axis direction. The first detector 41 detects the intensity of light output from the first filter 31. The second detector 42 detects the intensity of light output from the second filter 32. It is preferable that the losses in the respective wavelengths of the first filter 31 and the second filter 32 are complementary with each other.

Figure 4:
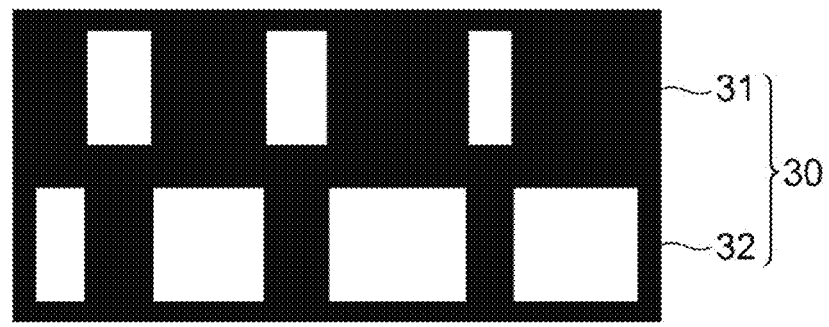
FIG. 4 is a diagram of an example of a spatial filter unit 30.

FIG. 4 is a diagram of an example of the spatial filter unit 30. In FIG. 4, the magnitude of the transmittance is illustrated in black and white, and a white region transmits light, and a black region blocks the light. For example, it is assumed that a range of a half-value width including each absorption peak wavelength in the absorption spectrum of the component in the measurement sample 90 be the absorption band, and that a range other than that be the non-absorption band. Regarding the first filter 31, it is assumed that the transmittance for the light in the non-absorption band of the component in the measurement sample 90 be 1 (or value close to 1) and that the transmittance for the light in the absorption band of the component be 0 (or value close to 0). Regarding the second filter 32, conversely, it is assumed that the transmittance for the light in the non-absorption band of the component in the measurement sample 90 be 0 (or value close to 0) and that the transmittance for the light in the absorption band of the component be 1 (or value close to 1).

Figure 5:
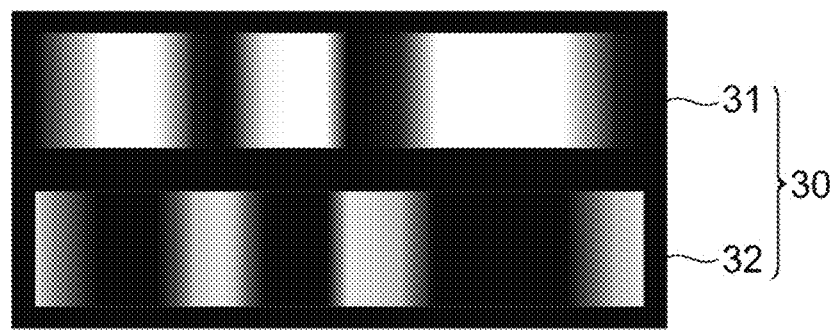
FIG. 5 is a diagram of another example of the spatial filter unit 30.

FIG. 5 is a diagram of another example of the spatial filter unit 30. In FIG. 5, the magnitude of the transmittance is expressed by tones, and when the color gets closer to white, the transmittance gets larger, and when the color gets closer to black, the transmittance gets smaller. In each wavelength, the smaller the absorption of the component in the measurement sample 90 is, the larger the transmittance of the first filter 31 is, and the smaller the transmittance of the second filter 32 is. Conversely, in each wavelength, the larger the absorption of the component in the measurement sample 90 is, the smaller the transmittance of the first filter 31 is, and the larger the transmittance of the second filter 32 is.

The losses in the respective wavelengths of the first filter 31 and the second filter 32 have the above relation, and therefore, the detection result (the intensity of the light which has passed through the first filter 31) P1 by the first detector 41 mainly depends on the intensity of the light in the non-absorption band of the component in the measurement sample 90, and the detection result (the intensity of the light which has passed through the second filter 32) P2 by the second detector 42 mainly depends on the intensity of the light in the absorption band of the component in the measurement sample 90. The spatial filter unit 30 (first filter 31 and second filter 32) is appropriately designed for each component (for example, a harmful substance and prohibited drug) to be determined in the measurement sample 90. The detection results P1 and P2 described above are in accordance with the kind and the concentration of the component in the measurement sample 90.

It is preferable that the analysis unit 50 use the detection result P1(0) by the first detector 41 and the detection result P2(0) by the second detector 42 in a case where the component is not contained in the measurement sample 90, when the component in the measurement sample 90 is evaluated based in the detection results P1 and P2. For example, it is preferable that the analysis unit 50 obtain the spectrum coincidence defined by the following formula (1), and evaluate the measurement sample 90 with respect to the component based on the spectrum coincidence.

$$\text{SPECTRUM COINCIDENCE} = \frac{P1}{P1(0)} - \frac{P2}{P2(0)} \quad (1)$$

In the present embodiment, by using both the first filter 31 and the second filter 32, the measurement sample 90 can be evaluated with higher sensitivity than a case where one of them is used, and further, a discrimination ability can be more improved. For example, when a component A having a specific transmission wavelength and a component B which transmits all wavelengths are measured, the detection results for the components A and B by the detector are the same in a case where the transmission wavelength of the filter coincides with the transmission wavelength of the component A. However, in the present embodiment, the detection results for the component A and the component B which are different from each other can be obtained by using the first filter 31 and the second filter 32.

The spatial filter unit 30 is appropriately designed for each component to be discriminated in the measurement sample 90. Therefore, when the magnitude of the loss which is applied to the light in each wavelength by the spatial filter unit 30 is fixed, the spatial filter units 30 which have been designed for the respective components to be discriminated are prepared, and the spatial filter units 30 are sequentially arranged in the optical path for measurement, and thus, each component in the measurement sample 90 can be evaluated.

On the other hand, the magnitude of the loss which is applied to the light in each wavelength by the spatial filter unit 30 may be variable. In this case, filter characteristics for each component to be discriminated is previously obtained and stored in a storage unit, and the filter characteristics are sequentially read from the storage unit and presented in the spatial filter unit 30 for measurement, and thus, each component of the measurement sample 90 can be evaluated.

Figure 6:
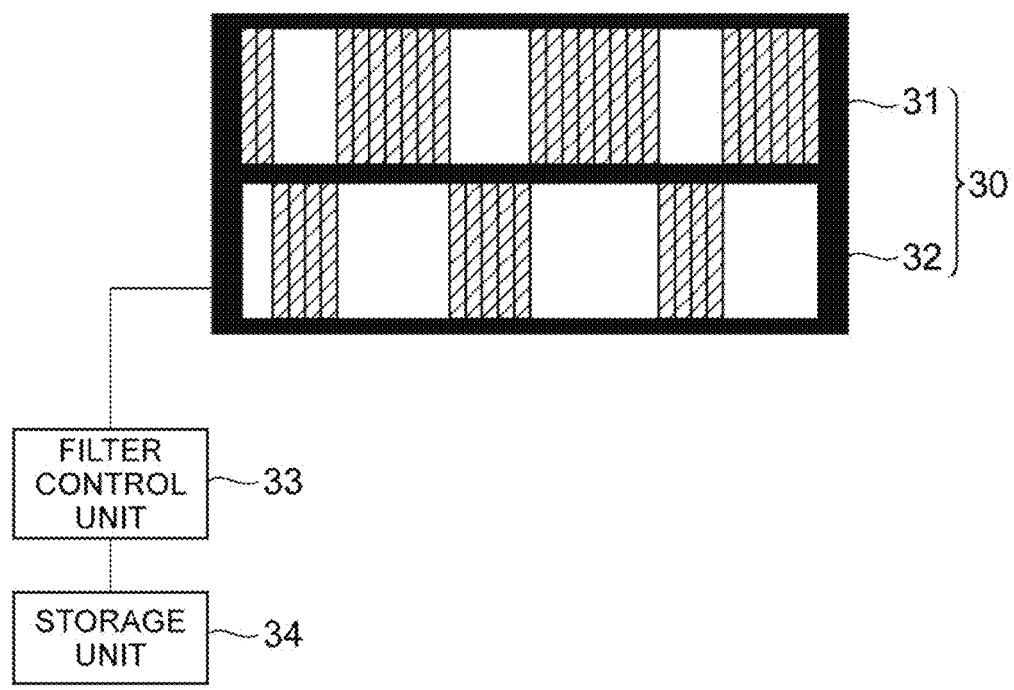
FIG. 6 is a diagram of a configuration of the spatial filter unit 30 by using a mechanical shutter array.

The spatial filter unit 30 having variable filter characteristics can be realized by a liquid crystal shutter, a mechanical shutter, and the like. FIG. 6 is a diagram of a configuration of the spatial filter unit 30 by using a mechanical shutter array.

The spatial filter unit 30 has a plurality of strip shutters arranged in parallel, and the respective strip shutters are arranged on one of the sides of the first filter 31 and the second filter 32 so that the transmission characteristics of the first filter 31 and the second filter 32 can be set. A storage unit 34 stores the filter characteristics obtained for each component to be determined. A filter control unit 33 sequentially reads the filter characteristics stored in the storage unit 34 and makes the spatial filter unit 30 present them. The spatial filter unit 30 having this configuration can easily realize the first filter 31 and the second filter 32 having the complementary transmission characteristics.

Further, a pair of the first filter 31 and the second filter 32 as described above can be realized for each component in time series by using the spatial filter unit 30 having variable filter characteristics. Further, the first filter 31 and the second filter 32 for each component can be realized in time series. In this case, it is sufficient that the detection unit 40 include a single detector, and a normal lens can be used instead of the cylindrical lenses 62 and 63.

Further, the spatial filter unit 30 may selectively apply loss to the light in one band of the absorption band and the non-absorption band of the component in the measurement sample 90. In this case, the detection unit 40 detects the intensity of the light in one band. The analysis unit 50 can obtain the intensities of the light in the absorption band and the light in the non-absorption band of the component based on the intensity of the light in both the absorption band and the non-absorption band of the component obtained by using other method and the detection result by the detection unit 40. The methods for obtaining the intensity of the light in both the absorption band and the non-absorption band of the component include first means for obtaining the intensity by transmitting the light in all bands in the spatial filter unit 30, second means for obtaining a sum of the intensities of the light in both the absorption band and the non-absorption band of the other component, third means for obtaining the intensity by branching a part of the light before the spatial filter unit 30, and the like.

Figure 7:
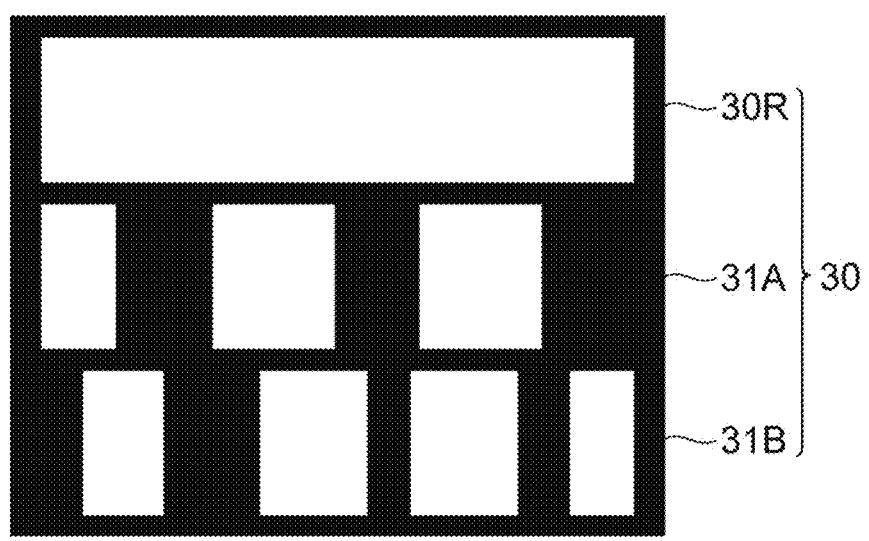
FIG. 7 is a diagram of an example of the spatial filter unit 30 used in a case where two components in a measurement sample 90 are evaluated.

FIG. 7 is a diagram of an example of the spatial filter unit 30 used in a case where two components in the measurement sample 90 are evaluated. The spatial filter unit 30 illustrated in FIG. 7 includes a reference filter 30R, a first filter 31A for the component A, and a first filter 31B for the component B. The reference filter 30R realizes the above-described first means and transmits the light in all the bands. The light in the non-absorption band of the component A passes through the first filter 31A for the component A. The light in the non-absorption band of the component B passes through a first filter 31B for the component B.

By using the spatial filter unit 30 described above, the analysis unit 50 can obtain the intensity $P_{total}$ of light, which has passed through the reference filter 30R, in all the bands detected by the detector, the intensity $P1_A$ of light, which has passed through the first filter 31A for the component A, in the non-absorption band of the component A detected by the detector, and the intensity $P1_B$ of light, which has passed through the first filter 31B for the component B, in the non-absorption band of the component B detected by the detector.

The analysis unit 50 can obtain the intensity $P2_A$ ($=P_{total}-P1_A$) of the light in the absorption band of the component A by subtracting the intensity $P1_A$ of the light in the non-absorption band of the component A from the intensity $P_{total}$ of the light in all the bands. Further, the analysis unit 50 can obtain the intensity $P2_B$ ($=P_{total}-P1_B$) of the light in the absorption band of the component B by subtracting the intensity $P1_B$ of the light in the non-absorption band of the component B from the intensity $P_{total}$ of the light in all the bands. The analysis unit 50 can evaluate the components A and B in the measurement sample 90 based on these light intensities.

Further, to realize the above-described second means, for example, the spatial filter unit 30 can include the first filter 31A and the second filter 32A for the component A and the first filter 31B for the component B. In this case, the analysis unit 50 can obtain the intensity $P1_A$ of the light, which has passed through the first filter 31A for the component A, in the non-absorption band of the component A detected by the detector, the intensity $P2_A$ of the light, which has passed through the second filter 32A for the component A, in the absorption band of the component A detected by the detector, and the intensity $P1_B$ of the light, which has passed through the first filter 31B for the component B, in the non-absorption band of the component B detected by the detector.

The analysis unit 50 can obtain the sum $P_{total}$ ($=P1_A+P2_A$) of the intensity $P1_A$ of the light in the non-absorption band of the component A and the intensity $P2_A$ of the light in the absorption band of the component A. In addition, the analysis unit 50 can obtain the intensity $P2_B$ ($=P_{total}-P1_B$) of the light in the absorption band of the component B by subtracting the intensity $P1_B$ of the light in the non-absorption band of the component B from the sum $P_{total}$. The analysis unit 50 can evaluate the components A and B in the measurement sample 90 based on these light intensities.

According to the first or second means described above, in order to evaluate N components (N is an integer of two or more) in the measurement sample 90, in general, the spatial filter unit 30 can include (N+1) filters. When the magnitude of the loss applied to the light in each wavelength by the spatial filter unit 30 is variable, the spatial filter unit 30 can be more downsized, and also, the number of detectors included in the detection unit 40 can be reduced.

Figure 8:
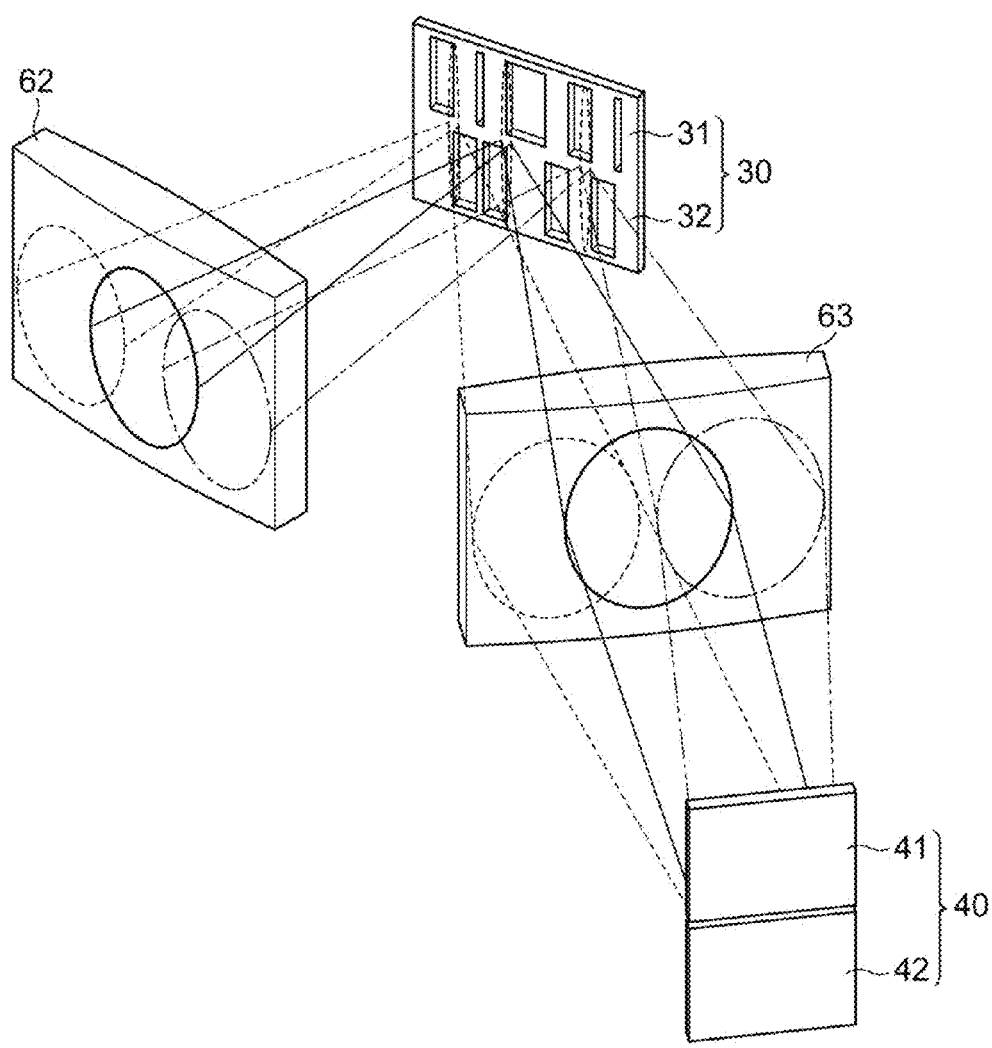
FIG. 8 is a perspective view of a part of the configuration of the spectroscopic measurement apparatus 1 in a case where a reflection type spatial filter unit 30 is used.

The spatial filter unit 30 may be a reflection type unit. FIG. 8 is a perspective view of a part of the configuration of the spectroscopic measurement apparatus 1 in a case where the reflection type spatial filter unit 30 is used. When the spatial filter unit 30 is a reflection type unit, the first filter 31 selectively reflects the light in the non-absorption band of the component in the measurement sample 90 and selectively absorbs the light in the absorption band of the component. The second filter 32 selectively absorbs the light in the non-absorption band of the component in the measurement sample 90 and selectively reflects the light in the absorption band of the component.

Reflection characteristics of the reflection type spatial filter unit 30 may be fixed and may be variable. When the reflection characteristics is variable, a liquid crystal and a DMD (Digital Micromirror Device) can configure the spatial filter unit 30. Further, when the reflection type spatial filter unit 30 is used, the spatial filter unit 30 can include (N+1) filters to evaluate the N components in the measurement sample 90.

As described above, in the present embodiment, spatial spectroscopy by the diffraction grating 20 which is a spectroscopic unit is used, and light detection is performed by the detection unit 40 by using the spatial filter unit 30, and accordingly, since the number of detectors included in the detection unit 40 can be reduced, the apparatus can be inexpensively formed, and also, high-speed measurement can be performed.

Next, a content and result of simulation performed regarding the effect of the spectroscopic measurement apparatus 1 according to the present embodiment will be described. In the following description, the concentration of the component in the measurement sample and the wavelength are expressed in arbitrary units.

Figure 9:
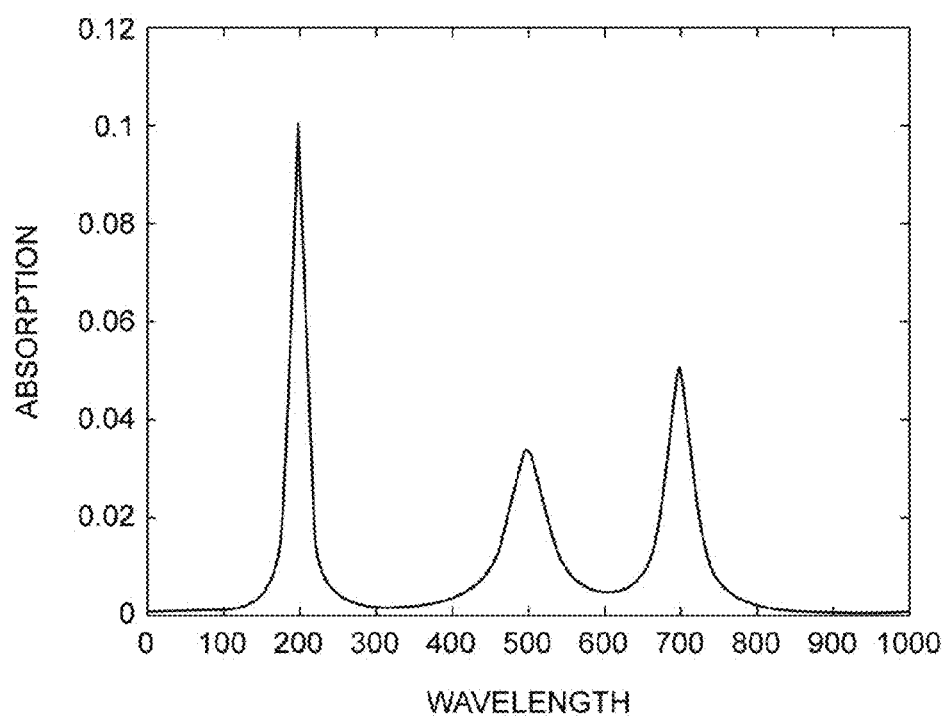
FIG. 9 is a diagram of an absorption spectrum of a component A.
Figure 10:
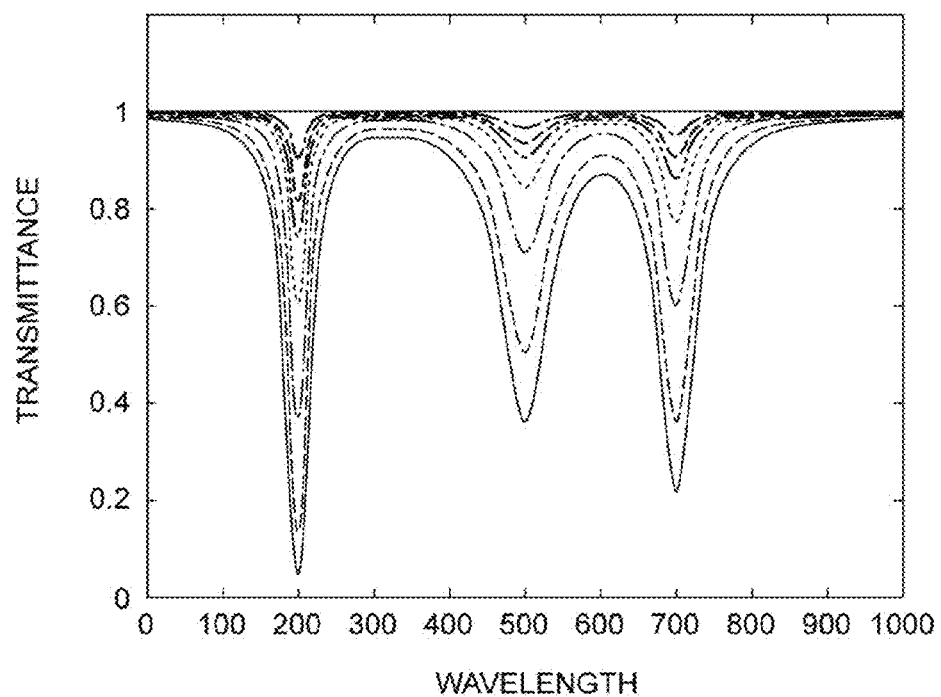
FIG. 10 is a diagram of a transmission spectrum of a measurement sample containing the component A.

FIG. 9 is a diagram of an absorption spectrum of the component A. FIG. 10 is a diagram of a transmission spectrum of the measurement sample containing the component A. The component A is set to have the absorption spectrum in which an absorption peak exists in each wavelength of 200, 500, and 700. It is assumed that the concentration of the component A in the measurement sample be each value of 0, 1, 2, 3, 5, 10, 20, and 30. Further, it is assumed that the output spectrum of the light source be flat over the entire wavelength region.

Figure 11:
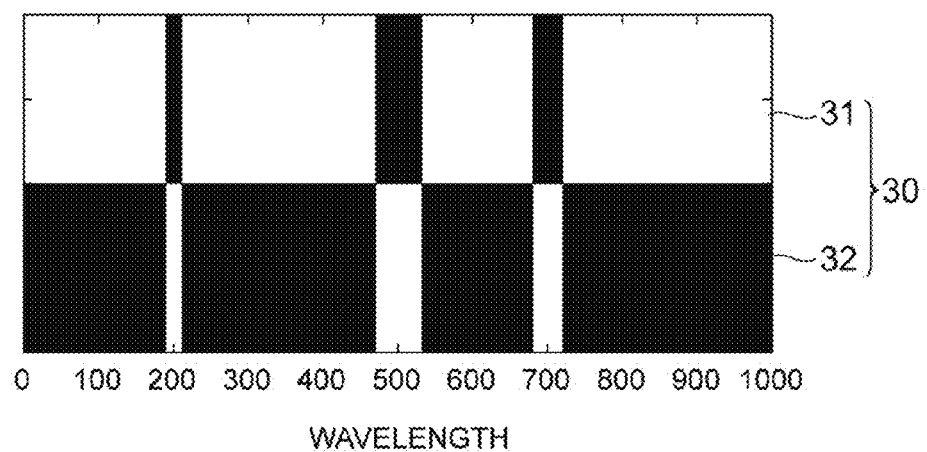
FIG. 11 is a diagram of a configuration of a spatial filter unit for the component A.

FIG. 11 is a diagram of a configuration of a spatial filter unit for the component A. In FIG. 11, the magnitude of the transmittance is illustrated in black and white, and a white region transmits light, and a black region blocks the light. It is assumed that a range of a half-value width including each absorption peak wavelength in the absorption spectrum of the component A in the measurement sample be the absorption band, and that the other range be the non-absorption band. Regarding the first filter 31, it is assumed that the transmittance for the light in the non-absorption band of the component A be 1, and that the transmittance for the light in the absorption band of the component A be 0. Regarding the second filter 32, conversely, it is assumed that the transmittance for the light in the non-absorption band of the component A be 0, and that the transmittance for the light in the absorption band of the component A be 1.

Figure 12:
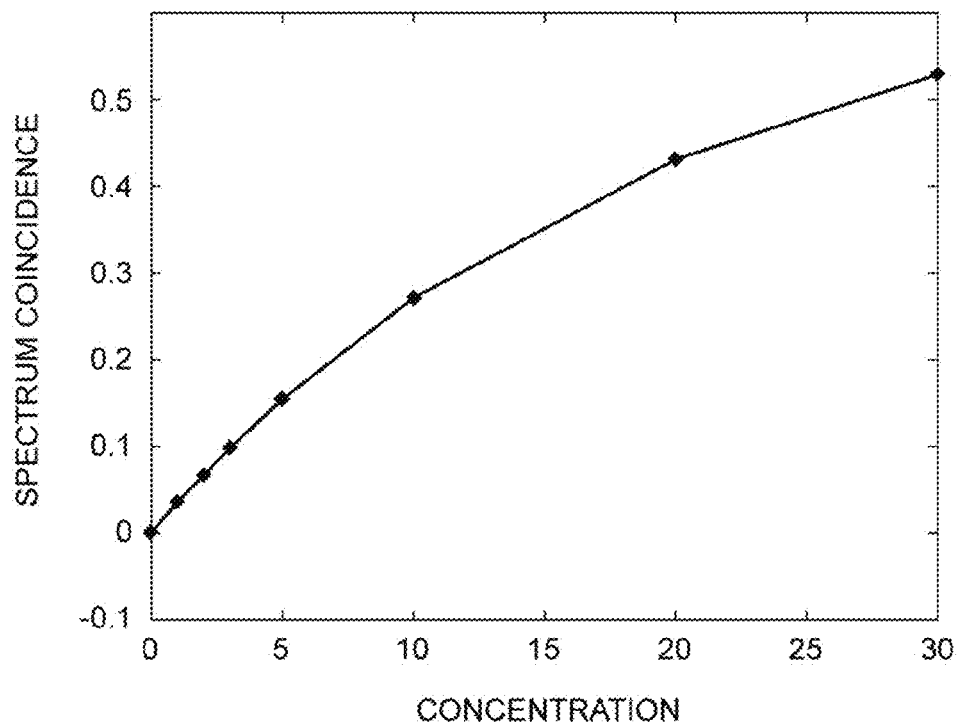
FIG. 12 is a graph of a relation between a spectrum coincidence and a concentration of the component A.

Under the above conditions, the detection result (the intensity of the light which has passed through the first filter 31) P1 by the first detector 41 and the detection result (the intensity of the light which has passed through the second filter 32) P2 by the second detector 42 are obtained, and the spectrum coincidence (above-described formula (1)) is calculated. FIG. 12 is a graph of a relation between a spectrum coincidence and a concentration of the component A. As illustrated in FIG. 12, the higher the concentration of the component A is, the larger the spectrum coincidence is.

Figure 13:
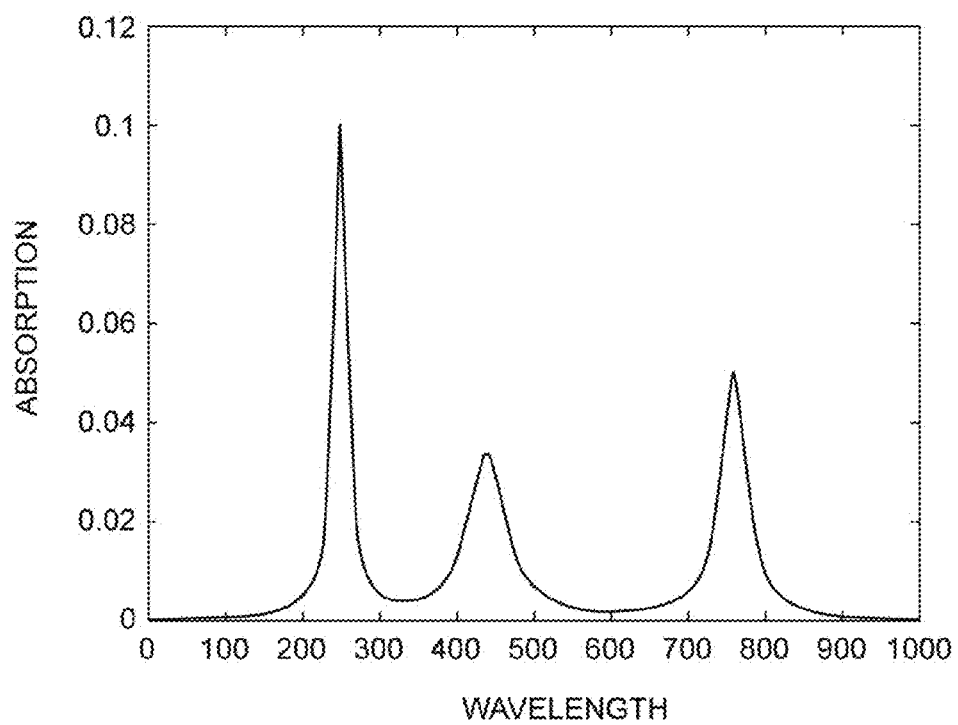
FIG. 13 is a diagram of an absorption spectrum of a component B.
Figure 14:
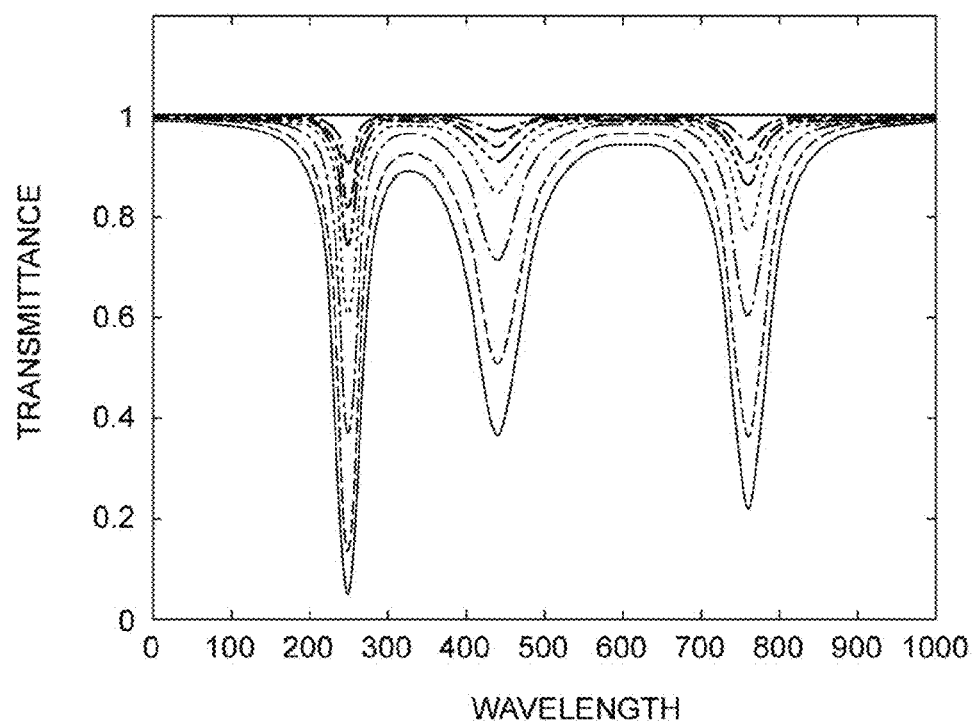
FIG. 14 is a diagram of a transmission spectrum of a measurement sample containing the component B.
Figure 15:
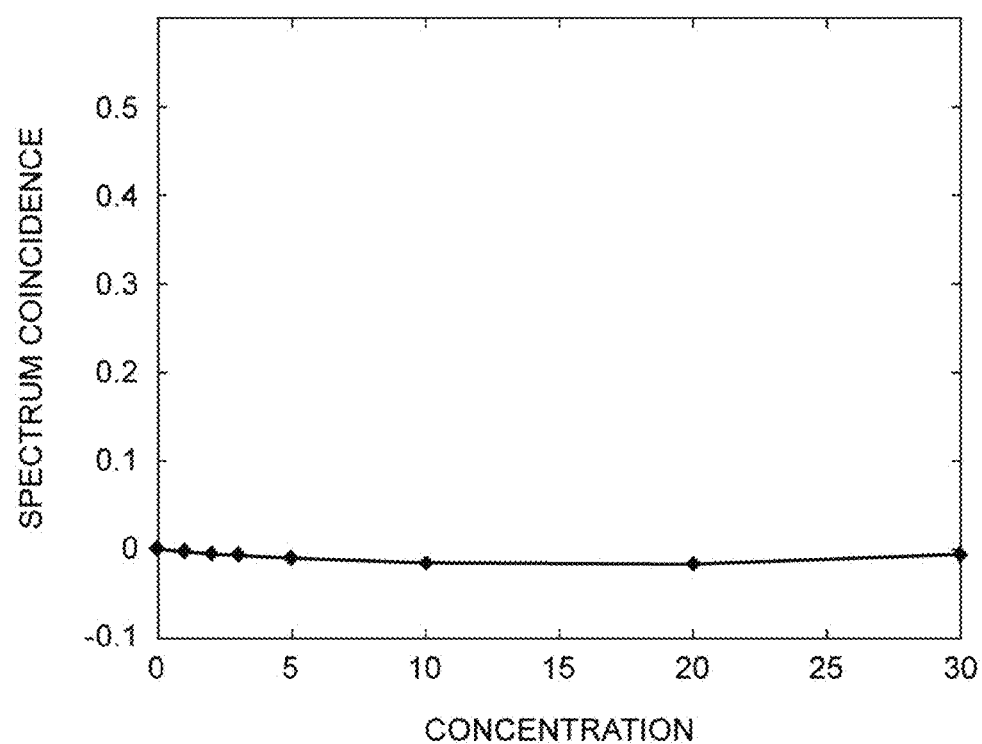
FIG. 15 is a graph of a relation between a spectrum coincidence and a concentration of the component B in a case where the spatial filter unit for the component A is used.

FIG. 13 is a diagram of an absorption spectrum of the component B. FIG. 14 is a diagram of a transmission spectrum of the measurement sample containing the component B. The component B is different from the component A, and is set to have the absorption spectrum in which an absorption peak exists in each wavelength of 250, 440, and 760. It is assumed that the concentration of the component B in the measurement sample be each value of 0, 1, 2, 3, 5, 10, 20, and 30. Further, it is assumed that the output spectrum of the light source be flat over the entire wavelength region. The spatial filter unit for the component A illustrated in FIG. 11 is used. FIG. 15 is a graph of a relation between a spectrum coincidence and a concentration of the component B in a case where the spatial filter unit for the component A is used. As illustrated in FIG. 15, when the component B is evaluated by using the spatial filter unit for the component A, the spectrum coincidence becomes a negative value.

Figure 16:
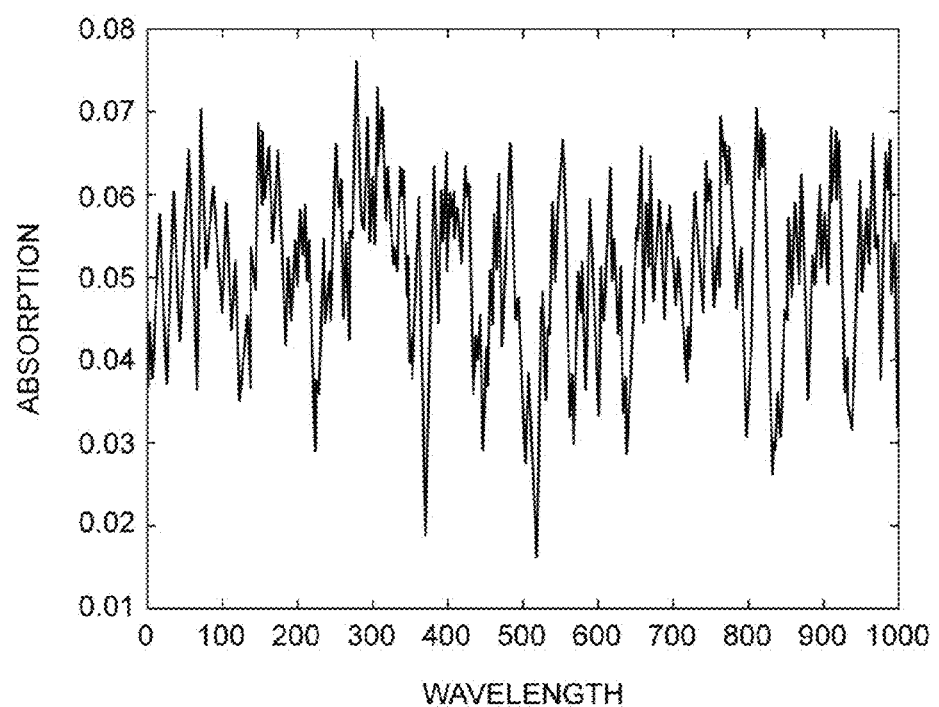
FIG. 16 is a diagram of an absorption spectrum of a component X.
Figure 17:
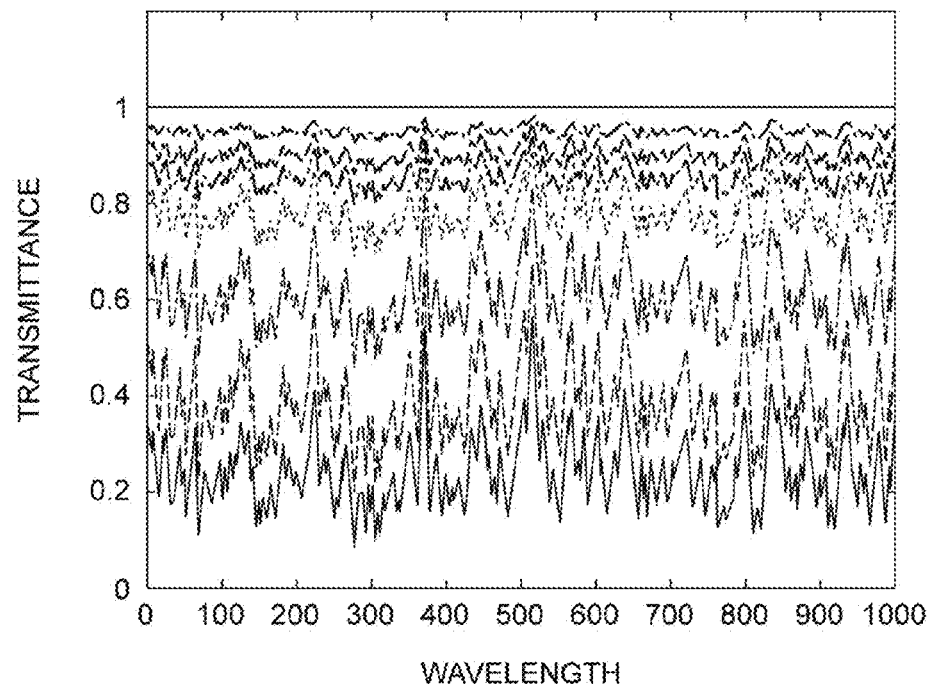
FIG. 17 is a diagram of a transmission spectrum of a measurement sample containing the component X.
Figure 18:
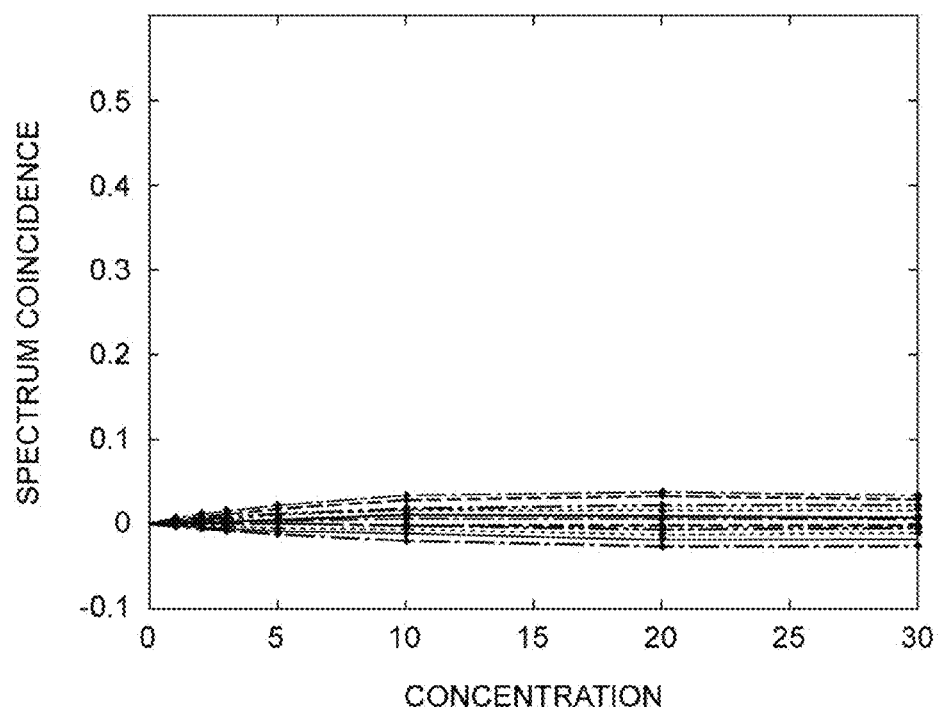
FIG. 18 is a graph of a relation between a spectrum coincidence and a concentration of the component X in a case where the spatial filter unit for the component A is used.

FIG. 16 is a diagram of an absorption spectrum of a component X. FIG. 17 is a diagram of a transmission spectrum of the measurement sample containing the component X. The component X is different from both the components A and B, and it is assumed that the component X have a random absorption spectrum. It is assumed that the concentration of the component X in the measurement sample be each value of 0, 1, 2, 3, 5, 10, 20, and 30. Further, it is assumed that the output spectrum of the light source be flat over the entire wavelength region. The spatial filter unit for the component A illustrated in FIG. 11 is used. FIG. 18 is a graph of a relation between the spectrum coincidence and the concentration of the component X in a case where the spatial filter unit for the component A is used. 20 kinds of the random absorption spectra of the component X are set, and the relation between the spectrum coincidence and the concentration of the component X is obtained for each case. As illustrated in FIG. 18, when the component X is evaluated by using the spatial filter unit for the component A, it has been found that the average of the spectrum coincidences is a value of 0, and the spectrum coincidence becomes a positive or negative small value.

Figure 19:
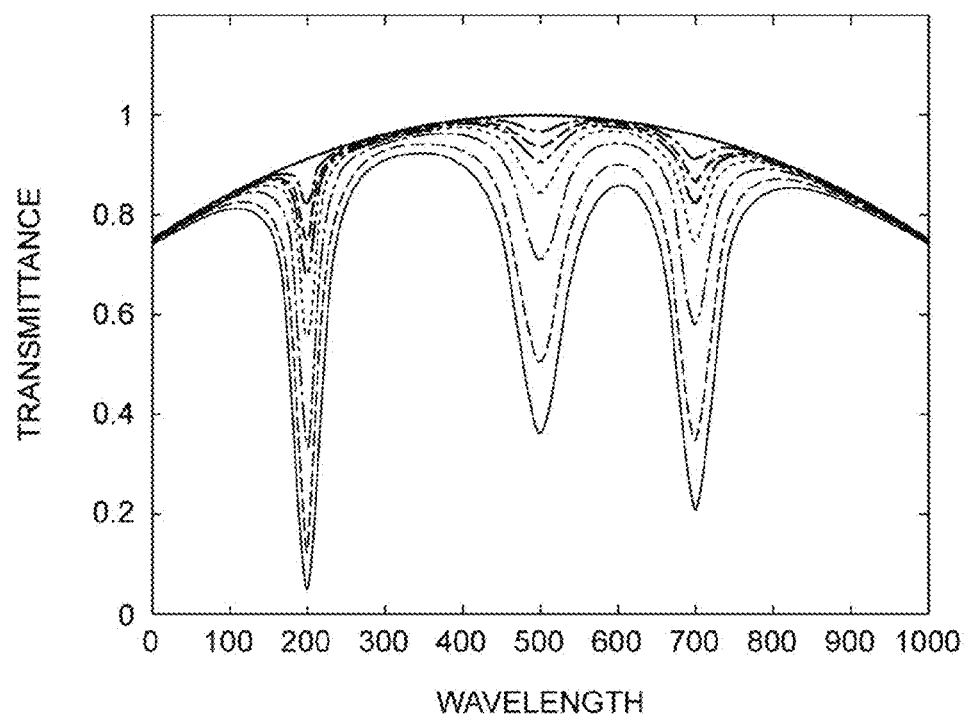
FIG. 19 is a diagram of a transmission spectrum of the measurement sample containing the component A in a case where an output spectrum of a light source is not flat.
Figure 20:
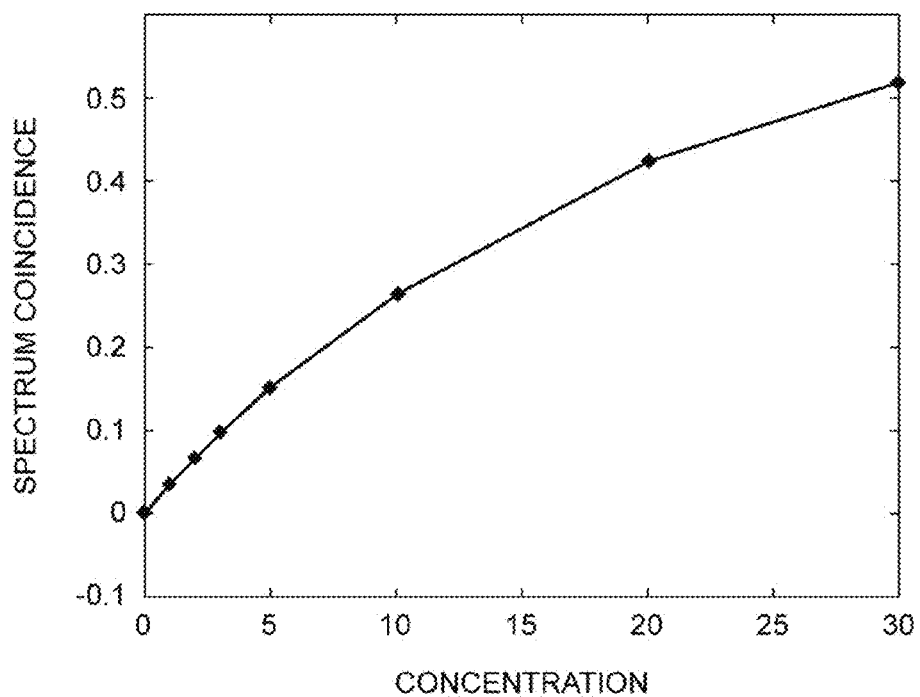
FIG. 20 is a graph of a relation between the spectrum coincidence and the concentration of the component A in a case where the output spectrum of the light source is not flat.

FIG. 19 is a diagram of the transmission spectrum of the measurement sample containing the component A in a case where the output spectrum of the light source is not flat. The absorption spectrum of the component A is as illustrated in FIG. 9. It is assumed that the concentration of the component A in the measurement sample be each value of 0, 1, 2, 3, 5, 10, 20, and 30. Further, it is assumed that the intensity of output light of the light source be large at the center of the band and be small at peripheries of the band. The spatial filter unit for the component A illustrated in FIG. 11 is used. FIG. 20 is a graph of a relation between the spectrum coincidence and the concentration of the component A in a case where the output spectrum of the light source is not flat. FIG. 20 indicates the result which is almost the same as that in FIG. 12 in a case where the output spectrum of the light source is flat. That is, it is understood that dependency to the shape of the output spectrum of the light source is small.

As understood from the above simulation results, the component A in the measurement sample can be selectively evaluated by using the spatial filter unit for the component A, without depending on the shape of the output spectrum of the light source. For example, a certain threshold value is previously set, and when the spectrum coincidence is larger than the threshold value, it can be determined that the component A is contained in the measurement sample.

Next, a content and result of simulation performed regarding the effect of the spectroscopic measurement apparatus 1 according to the present embodiment in a case where a plurality of components is contained in the measurement sample will be described. Also in the following description, the concentration of each component in the measurement sample and the wavelength are expressed in arbitrary units.

Figure 21:
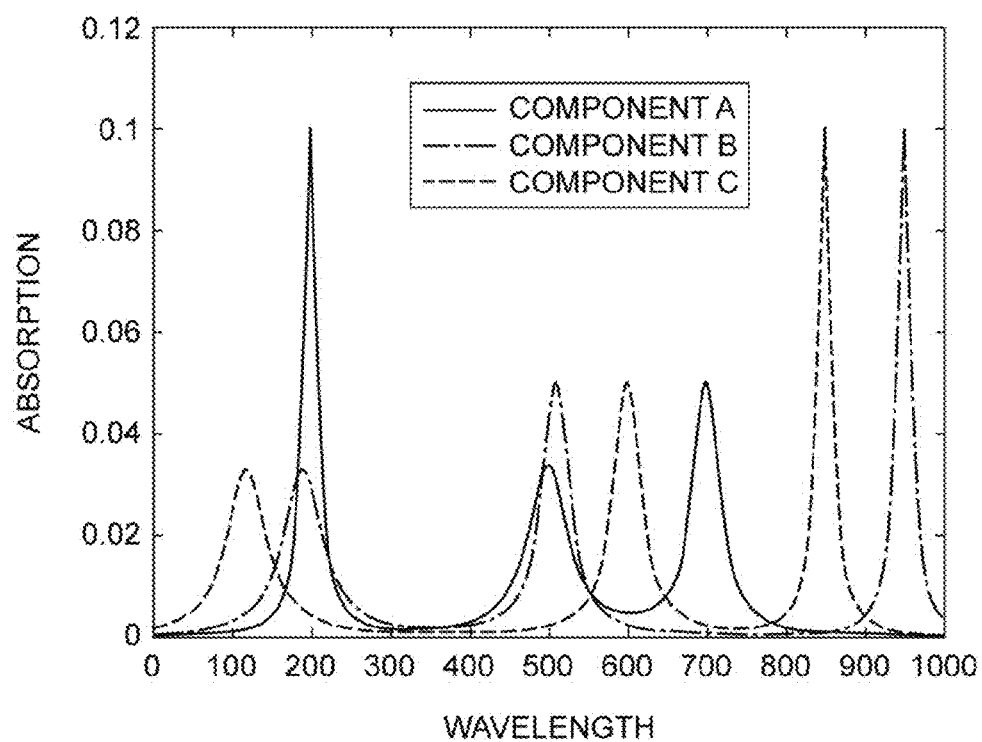
FIG. 21 is a diagram of absorption spectra of the respective components A, B, and C.
Figure 22:
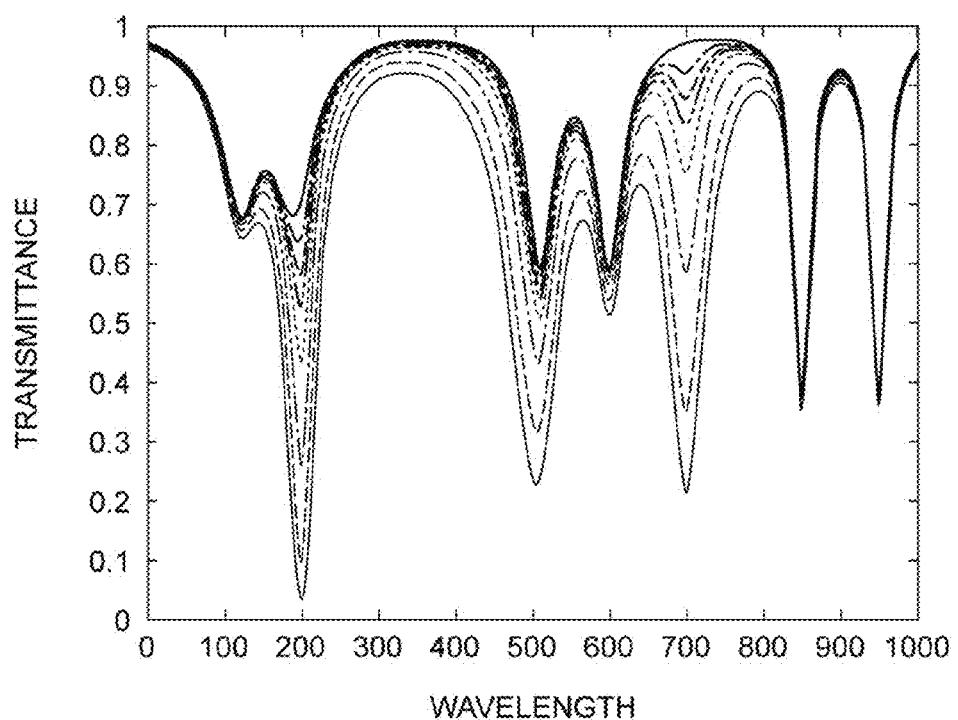
FIG. 22 is a diagram of transmission spectra of the measurement sample containing the components A, B, and C.

FIG. 21 is a diagram of absorption spectra of the respective components A, B, and C. The absorption spectrum of the component A from among the above absorption spectra is the same as that illustrated in FIG. 9. The absorption spectra of the respective components A, B, and C are different from each other. The transmission spectrum of the measurement sample containing the components A, B, and C has a more complex shape compared to the transmission spectrum of the measurement sample containing any one of the components. The transmission spectrum of the measurement sample containing only the component A is as illustrated in FIG. 10, whereas, the transmission spectrum of the measurement sample containing the components A, B, and C is as illustrated in FIG. 22. In FIG. 22, it is assumed that the concentration of the component A in the measurement sample be each value of 0, 1, 2, 3, 5, 10, 20, and 30, and that the concentration of each components B and C be 10. Further, it is assumed that the output spectrum of the light source be flat over the entire wavelength region.

Figure 23:
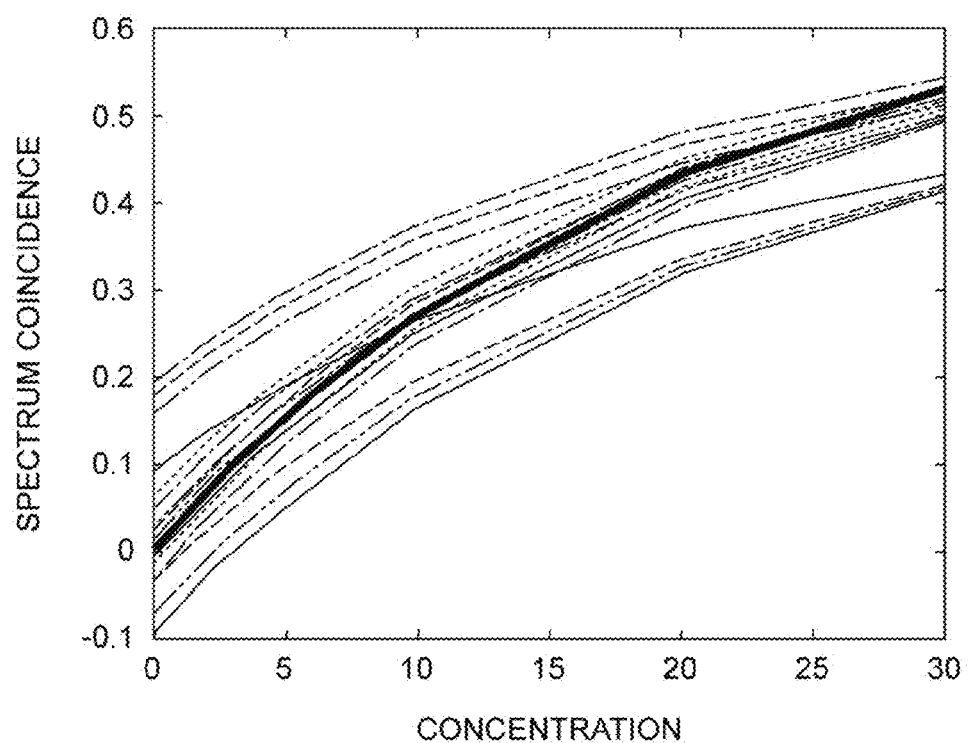
FIG. 23 is a graph of a relation between the spectrum coincidence and the concentration of the component A in a case where the spatial filter unit for the component A is used.

FIG. 23 is a graph of a relation between the spectrum coincidence and the concentration of the component A in a case where the spatial filter unit for the component A is used. The spatial filter unit for the component A is as illustrated in FIG. 11. It is assumed that the concentration of the component A in the measurement sample be each value of 0, 1, 2, 3, 5, 10, 20, and 30, that the concentration of the component B be each value of 0, 2, 5, and 20, and that the concentration of the component C be each value of 0, 2, 5, and 20. In FIG. 23, the graph expressed by a thick line indicates the relation between the spectrum coincidence and the concentration of the component A in a case where both the components B and C are not contained. The graphs expressed by lines other than the thick line indicate the relation between the spectrum coincidence and the concentration of the component A in a case where the component B or C is contained.

According to FIG. 23, the spectrum coincidence obtained for the component A to be evaluated is any one of overestimation and underestimation according to the kind of other component contained in the measurement sample other than the component A. When the absorption spectrum of the other component is similar to the absorption spectrum of the component A, the spectrum coincidence is in overestimation. On the other hand, when the absorption spectrum of the other component is different from the absorption spectrum of the component A, the spectrum coincidence is in underestimation.

Figure 24:
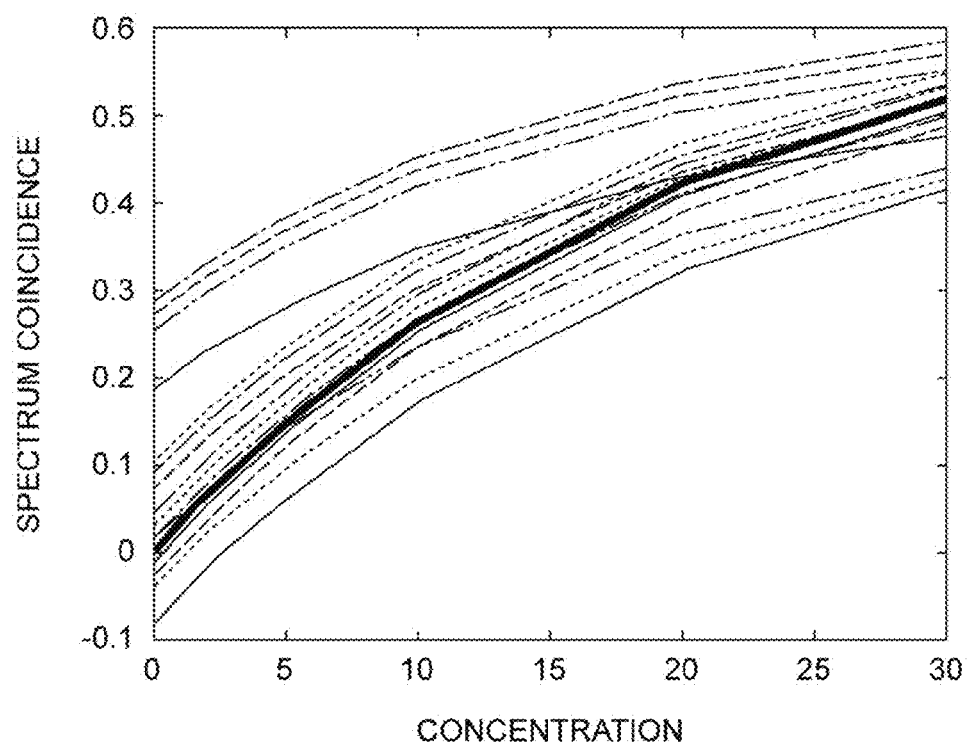
FIG. 24 is a graph of a relation between the spectrum coincidence and the concentration of the component B in a case where the spatial filter unit for the component B is used.

FIG. 24 is a graph of a relation between the spectrum coincidence and the concentration of the component B in a case where the spatial filter unit for the component B is used. The spatial filter unit for the component B is designed similarly to the spatial filter unit for the component A. It is assumed that the concentration of the component B in the measurement sample be each value of 0, 1, 2, 3, 5, 10, 20, and 30, that the concentration of the component A be each value of 0, 2, 5, and 20, and that the concentration of the component C be each value of 0, 2, 5, and 20. In FIG. 24, the graph expressed by a thick line indicates the relation between the spectrum coincidence and the concentration of the component B in a case where both the components A and C are not contained. The graphs expressed by lines other than the thick line indicate the relation between the spectrum coincidence and the concentration of the component B in a case where the component A or C is contained.

Figure 25:
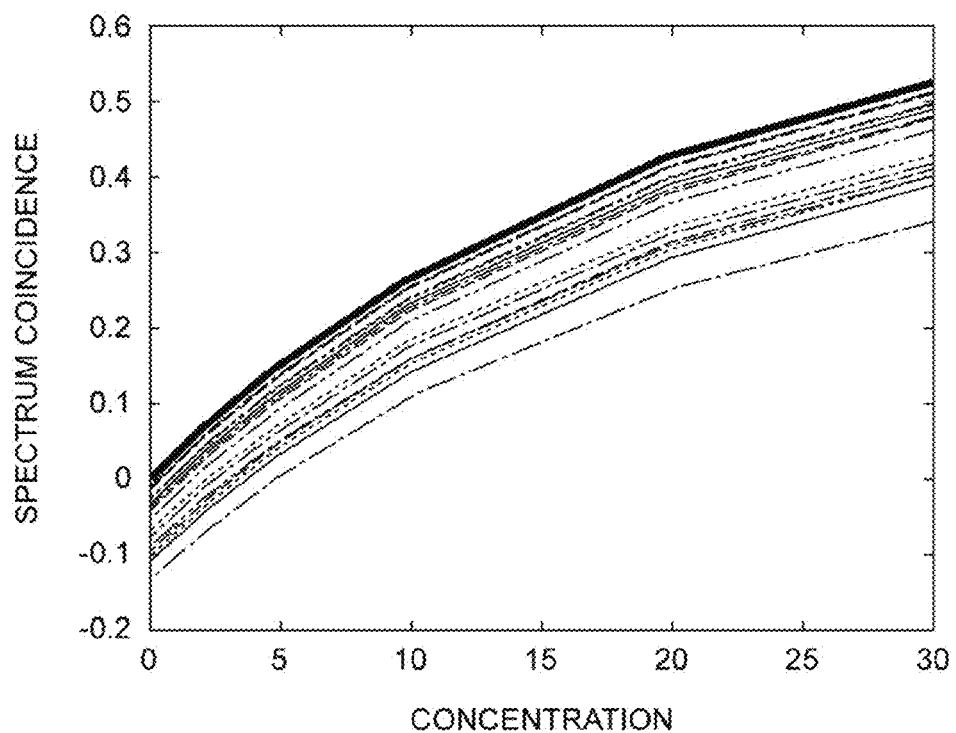
FIG. 25 is a graph of a relation between a spectrum coincidence and a concentration of the component C in a case where the spatial filter unit for the component C is used.

FIG. 25 is a graph of a relation between the spectrum coincidence and the concentration of the component C in a case where a spatial filter unit for the component C is used. The spatial filter unit for the component C is designed similarly to the spatial filter unit for the component A. It is assumed that the concentration of the component C in the measurement sample be each value of 0, 1, 2, 3, 5, 10, 20, and 30, that the concentration of the component A be each value of 0, 2, 5, and 20, and that the concentration of the component B be each value of 0, 2, 5, and 20. In FIG. 25, the graph expressed by a thick line indicates the relation between the spectrum coincidence and the concentration of the component C in a case where both the components A and B are not contained. The graphs expressed by lines other than the thick line indicate the relation between the spectrum coincidence and the concentration of the component C in a case where the component A or B is contained.

As illustrated in FIG. 21, the absorption spectrum of the component C has low similarity to the respective absorption spectra of the components A and B. Therefore, as illustrated in FIG. 25, when the measurement sample contains the components A and B, the spectrum coincidence for the component C is in underestimation.

As described above, when the plurality of components are contained in the measurement sample, the spectrum coincidence obtained for each component is inaccurate. Therefore, it is preferable that following correction be performed. A point to be considered in performing the correction is that the measurement performed by using the spatial filter unit for the component A has not only a sensitivity for the absorption spectrum of the component A, but also a positive or negative sensitivity for the absorption spectrum of the other component.

A sensitivity at the time when a j-th component of the N components is spectroscopically measured by a spatial filter unit for an i-th component of the N components is represented by $a_{i,j}$. A weighting coefficient of the spatial filter unit for the i-th component is represented by $K_i(\lambda)$. An absorption spectrum of the j-th component is represented by $L_j(\lambda)$. N is an integer of two or more, and i and j are respective integers of one or more and N or less. $\lambda$ is a wavelength.

The sensitivity $a_{i,j}$ can be expressed by the following formulas (2a) and (2b). The weighting coefficient $K_i(\lambda)$ is $-1/P1(0)$ in the non-absorption band and $1/P2(0)$ in the absorption band. $P1(0)$ and $P2(0)$ are parameters used also in the formula (1). Further, a sensitivity matrix A is expressed by the following formula (3) having the sensitivity $a_{i,j}$ as an element of i-th row and j-th column. The sensitivity matrix A can be previously obtained by calculation or measurement.

$$a_{i,j} = \int K_i(\lambda) \cdot L_j(\lambda) \cdot d\lambda \qquad (2a)$$

$$K_i(\lambda) = \begin{cases} -1/P1(0) & \text{(in transmission band)} \\ 1/P2(0) & \text{(in absorption band)} \end{cases} \qquad (2b)$$

$$A = \begin{pmatrix} a_{1,1} & a_{1,2} & \cdots & a_{1,N} \\ a_{2,1} & a_{2,2} & \cdots & a_{2,N} \\ \vdots & \vdots & & \vdots \\ a_{N,1} & a_{N,2} & \cdots & a_{N,N} \end{pmatrix} \qquad (3)$$

A true spectrum coincidence for the i-th component is assumed to be $s_{true\_i}$, and a true spectrum coincidence vector $S_{true}$ is expressed by the following formula (4) having $s_{true\_i}$ as the i-th element. Further, an apparent spectrum coincidence obtained by the measurement for the i-th component is assumed to be $s_i$, and an apparent spectrum coincidence vector S is expressed by the following formula (5) having $s_i$ as the i-th element.

$$S_{true} = \begin{pmatrix} s_{true\_1} \\ s_{true\_2} \\ \vdots \\ s_{true\_N} \end{pmatrix} \quad (4)$$

$$S = \begin{pmatrix} s_1 \\ s_2 \\ \vdots \\ s_N \end{pmatrix} \quad (5)$$

The apparent spectrum coincidence vector S is expressed as the following formula (6) by using the sensitivity matrix A and the true spectrum coincidence vector $S_{true}$. Therefore, the true spectrum coincidence vector $S_{true}$ is expressed as the following formula (7). In this way, it is preferable that the analysis unit 50 obtain the true spectrum coincidence $s_{true\_i}$ by correcting the evaluation result (apparent spectrum coincidence $s_i$) for the i-th component by the spatial filter unit for the i-th component based on the sensitivity $a_{i,j}$.

$$S = A S_{true} \quad (6)$$

$$S_{true} = A^{-1} S \quad (7)$$

Figure 26:
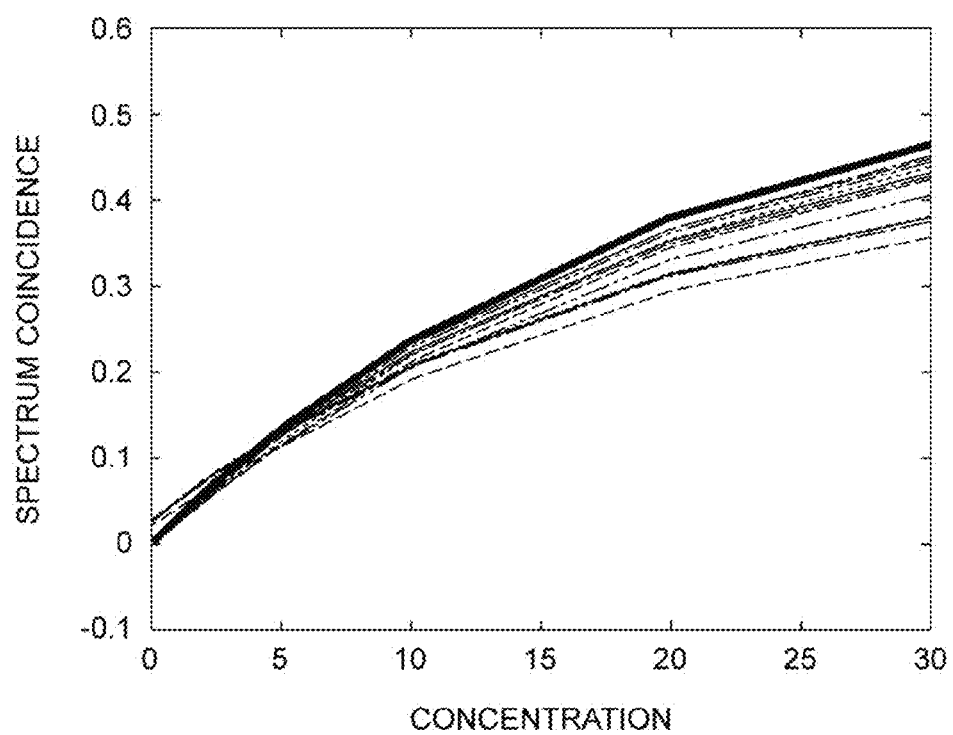
FIG. 26 is a graph of a relation between a corrected spectrum coincidence and the concentration of the component A in a case where the spatial filter unit for the component A is used.
Figure 27:
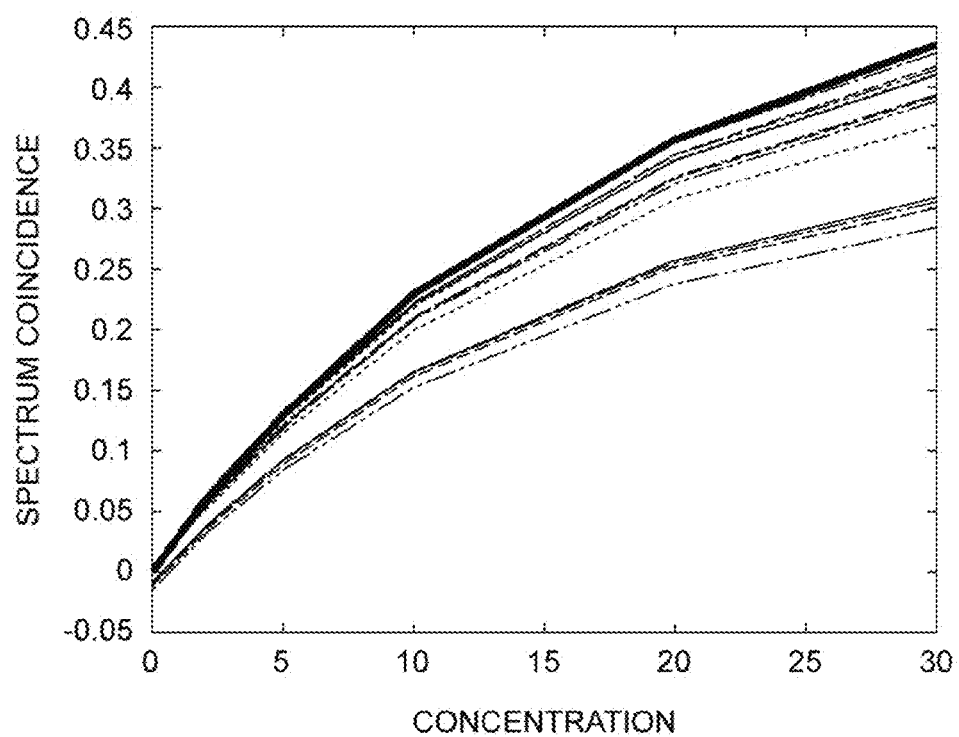
FIG. 27 is a graph of a relation between a corrected spectrum coincidence and the concentration of the component B in a case where the spatial filter unit for the component B is used.
Figure 28:
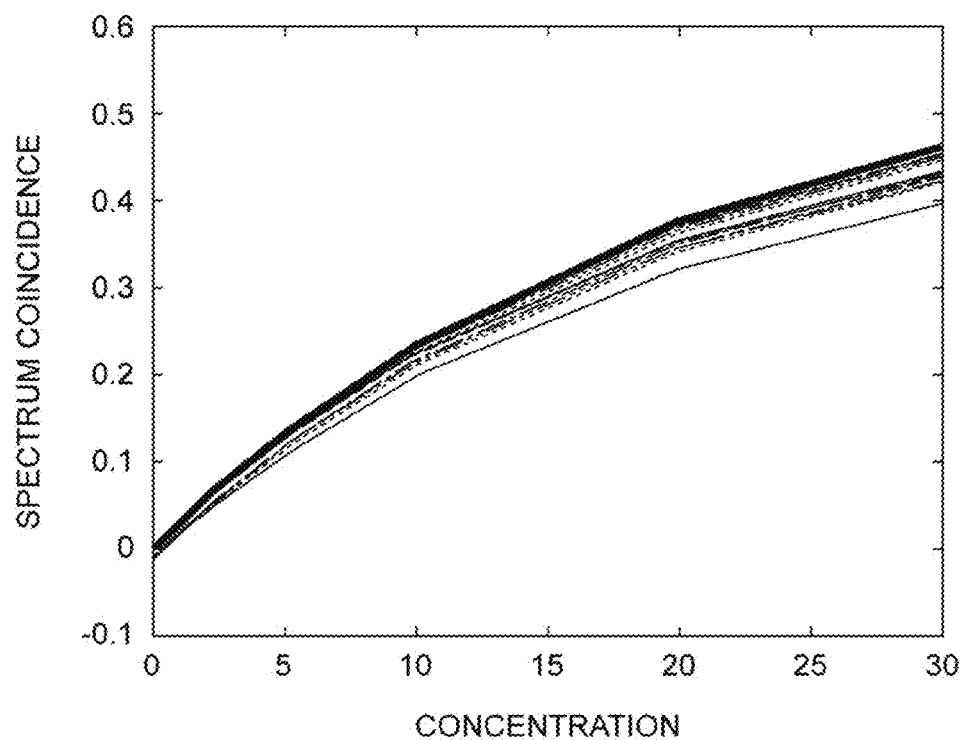
FIG. 28 is a graph of a relation between a corrected spectrum coincidence and the concentration of the component C in a case where the spatial filter unit for the component C is used.

In FIG. 26 to FIG. 28, results of the above-described correction for the apparent spectrum coincidences illustrated in FIG. 23 to FIG. 25 are illustrated.

FIG. 26 is a graph of a relation between a corrected spectrum coincidence and the concentration of the component A in a case where the spatial filter unit for the component A is used. In FIG. 26, the graph expressed by a thick line indicates the relation between the spectrum coincidence and the concentration of the component A in a case where both the components B and C are not contained. The graphs expressed by lines other than the thick line indicate the relation between the spectrum coincidence and the concentration of the component A in a case where the component B or C is contained.

FIG. 27 is a graph of a relation between a corrected spectrum coincidence and the concentration of the component B in a case where the spatial filter unit for the component B is used. In FIG. 27, the graph expressed by a thick line indicates the relation between the spectrum coincidence and the concentration of the component B in a case where both the components A and C are not contained. The graphs expressed by lines other than the thick line indicate the relation between the spectrum coincidence and the concentration of the component B in a case where the component A or C is contained.

FIG. 28 is a graph of a relation between a corrected spectrum coincidence and the concentration of the component C in a case where the spatial filter unit for the component C is used. In FIG. 28, the graph expressed by a thick line indicates the relation between the spectrum coincidence and the concentration of the component C in a case where both the components A and B are not contained. The graphs expressed by lines other than the thick line indicate the relation between the spectrum coincidence and the concentration of the component C in a case where the component A or B is contained.

It is understood that the dependency on the concentration of the component other than the component to be evaluated in the corrected spectrum coincidence illustrated in FIG. 26 to FIG. 28 is reduced compared to that in the spectrum coincidence before being corrected illustrated in FIG. 23 to FIG. 25. When the concentration of the component other than the component to be evaluated is high, the corrected spectrum coincidence tends to have a larger difference from a true value. However, in a range in which the concentration of the component to be evaluated is close to zero, the corrected spectrum coincidence has a small difference from the true value. This indicates that the component can be detected without worrying about false positive even when the concentration of the component to be evaluated is low.

The spectroscopic measurement apparatus according to the present invention is not limited to the embodiments and examples described above, and can be variously modified.

The spectroscopic measurement apparatus according to the embodiment includes (1) a light source which outputs light, (2) a spectroscopic unit which spatially disperses the light output from the light source, and outputs the light to different optical paths according to a wavelength, (3) a spatial filter unit which inputs the light output from the spectroscopic unit to different positions according to the wavelength, applies loss depending on the wavelength to the light, and outputs the light, (4) a detection unit which detects the intensity of the light output from the spatial filter unit, and (5) an analysis unit which obtains the respective intensities of light in an absorption band and light in a non-absorption band of a component in a measurement sample from among the light which has passed through or has been reflected by the measurement sample arranged on an optical path between the light source and the detection unit based on the detection result by the detection unit, and evaluates the measurement sample with respect to the component.

In the above-described spectroscopic measurement apparatus, it is preferable that the magnitude of the loss applied to the light in each wavelength by the spatial filter unit be variable. Further, in the above-described spectroscopic measurement apparatus, it is preferable that the spatial filter unit be set in time series to the first filter which selectively applies loss to the light in the absorption band of the component and the second filter which selectively applies loss to the light in the non-absorption band of the component. Further, in this case, it is preferable that the losses in the respective wavelengths in the first filter and the second filter are complementary with each other.

Further, in the above-described spectroscopic measurement apparatus, it is preferable that the spatial filter unit include the first filter which selectively applies the loss to the light in the absorption band of the component and the second filter which selectively applies the loss to the light in the non-absorption band of the component. Further, in this case, it is preferable that the losses in the respective wavelengths in the first filter and the second filter are complementary with each other.

Further, in the above-described spectroscopic measurement apparatus, it is preferable that the spatial filter unit selectively apply the loss to the light in one band of the absorption band and the non-absorption band of the component, and that the analysis unit obtain the respective intensities of the light in the absorption band and the light in the non-absorption band of the component based on the intensity of the light in both the absorption band and the non-absorption band of the component and the detection result by the detection unit.

Further, in the above-described spectroscopic measurement apparatus, it is preferable that the spatial filter unit be provided so as to correspond to each of N components (N is an integer of two or more) in the measurement sample, and that the analysis unit correct the evaluation result on the i-th component by the spatial filter unit for the i-th component based on the sensitivity in a case where the j-th component of N components is spectroscopically measured by the spatial filter unit for the i-th component of N components.

The present invention can be used as a spectroscopic measurement apparatus which can perform high-speed measurement with an inexpensive configuration.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A spectroscopic measurement apparatus comprising:
   a light source configured to output light;
   a spectroscopic unit configured to spatially disperse the light output from the light source, and output the light to different optical paths according to a wavelength;
   a spatial filter unit configured to input the light output from the spectroscopic unit to different positions according to the wavelength, apply loss depending on the wavelength to the light, and output the light, the spatial filter unit including a first filter configured to selectively apply loss to light in an absorption band of a component in a measurement sample and a second filter configured to selectively apply loss to light in a non-absorption band of the component;
   a detection unit including a first detector configured to detect the intensity of the light output from the first filter and a second detector configured to detect the intensity of the light output from the second filter; and
   an analysis unit configured to obtain the respective intensities of the light in the absorption band and the light in the non-absorption band of the component in the measurement sample in the light which has passed through or has been reflected by the measurement sample arranged on an optical path between the light source and the detection unit based on the detection result by the detection unit, and evaluate the component in the measurement sample.

2. The spectroscopic measurement apparatus according to claim 1, wherein a magnitude of the loss applied to the light in each wavelength by the spatial filter unit is variable.

3. The spectroscopic measurement apparatus according to claim 1, wherein the losses in the respective wavelengths of the first filter and the second filter are complementary with each other.

4. The spectroscopic measurement apparatus according to claim 1, wherein the spatial filter unit is provided so as to correspond to each of N components (N is an integer of two or more) in the measurement sample, and
   the analysis unit corrects the evaluation result on an i-th component by the spatial filter unit for the i-th component based on a sensitivity in a case where a j-th component of the N components is spectroscopically measured by the spatial filter unit for the i-th component of the N components.

5. A spectroscopic measurement apparatus comprising:
   a light source configured to output light;
   a spectroscopic unit configured to spatially disperse the light output from the light source, and output the light to different optical paths according to a wavelength;
   a spatial filter unit configured to input the light output from the spectroscopic unit to different positions according to the wavelength, apply loss depending on the wavelength to the light, and output the light, the spatial filter unit including a single filter by which a magnitude of the loss applied to the light in each wavelength is variable, and the single filter being set in time series to a first filter configured to selectively apply loss to light in an absorption band of a component in a measurement sample and a second filter configured to selectively apply loss to light in a non-absorption band of the component;
   a detection unit including a single detector configured to detect the intensity of the light output from the single filter; and
   an analysis unit configured to obtain the respective intensities of the light in the absorption band and the light in the non-absorption band of the component in the measurement sample in the light which has passed through or has been reflected by the measurement sample arranged on an optical path between the light source and the detection unit based on the detection result by the detection unit, and evaluate the component in the measurement sample.

6. The spectroscopic measurement apparatus according to claim 5, wherein the losses in the respective wavelengths of the first filter and the second filter are complementary with each other.

7. The spectroscopic measurement apparatus according to claim 5, wherein the spatial filter unit is provided so as to correspond to each of N components (N is an integer of two or more) in the measurement sample, and
   the analysis unit corrects the evaluation result on an i-th component by the spatial filter unit for the i-th component based on a sensitivity in a case where a j-th component of the N components is spectroscopically measured by the spatial filter unit for the i-th component of the N components.

8. A spectroscopic measurement apparatus comprising:
   a light source configured to output light;
   a spectroscopic unit configured to spatially disperse the light output from the light source, and output the light to different optical paths according to a wavelength;
   a spatial filter unit configured to input the light output from the spectroscopic unit to different positions according to the wavelength, apply loss depending on the wavelength to the light, and output the light, the spatial filter unit including a filter configured to selectively apply loss to light in one band of an absorption band and a non-absorption band of a component in a measurement sample;
   a detection unit including a detector configured to detect the intensity of the light output from the filter; and
   an analysis unit configured to obtain the respective intensities of the light in the absorption band and the light in the non-absorption band of the component in the measurement sample in the light which has passed through or has been reflected by the measurement sample arranged on an optical path between the light source and the detection unit based on the intensity of the light in both the absorption band and the non-absorption band of the component and the detection result by the detection unit, and evaluate the component in the measurement sample.

9. The spectroscopic measurement apparatus according to claim 8, wherein the spatial filter unit is provided so as to correspond to each of N components (N is an integer of two or more) in the measurement sample, and
   the analysis unit corrects the evaluation result on an i-th component by the spatial filter unit for the i-th component based on a sensitivity in a case where a j-th component of the N components is spectroscopically measured by the spatial filter unit for the i-th component of the N components.

* * * * *